US006458541B1

(12) United States Patent
Sklar et al.

(10) Patent No.: US 6,458,541 B1
(45) Date of Patent: Oct. 1, 2002

(54) BDNF POLYMORPHISM AND ASSOCIATION WITH BIPOLAR DISORDER

(75) Inventors: Pamela Sklar, Brookline; Eric S. Lander, Cambridge, both of MA (US); J. Raymond DePaulo, Baltimore; Melvin G. McInnis, Timonium, both of MD (US)

(73) Assignees: Whitehead Institute for Biomedical Research, Cambridge, MA (US); General Hospital Corporation, Boston, MA (US); Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/636,368

(22) Filed: Aug. 11, 2000

Related U.S. Application Data

(60) Provisional application No. 60/148,389, filed on Aug. 11, 1999.

(51) Int. Cl.[7] .............................. C12Q 1/68; C07K 1/00; A61K 38/24; A01N 37/18
(52) U.S. Cl. ........................... 435/6; 530/399; 530/350; 514/2; 514/12
(58) Field of Search ................................ 530/350, 399; 514/2, 12; 435/6

(56) References Cited

U.S. PATENT DOCUMENTS

| 5,235,043 A | 8/1993 | Collins et al. | ............. 530/399 |
|---|---|---|---|
| 5,606,031 A | 2/1997 | Lile et al. | ............. 530/416 |
| 5,986,070 A | 11/1999 | Collins et al. | ............. 530/404 |

FOREIGN PATENT DOCUMENTS

| EP | 0 450 386 A2 | 10/1991 | ........... C12N/15/12 |
|---|---|---|---|

OTHER PUBLICATIONS

Krebs, M. O. et al., "Association Study of Brain–Derived Neurotrophic Factor (BDNF) Polymorphism in Schizophrenia," *Am. J. Med. Genet.*, 81(6):520 (1998).

Leibrock, Joachim et al., "Molecular cloning and expression of brain–derived neurotrophic factor," *Nature*, 341:149–152 (1989).

Maisonpierre, Peter C. et al., "Neurotrophin–3: A Neurotrophic Factor Related to NGF and BDNF," *Science*, 247:1446–1451 (1990).

Hofer, Magdalena et al., "Regional distribution of brain-derived neurotrophic factor mRNA in the adult mouse brain," *The EMBO Journal*, 9 (8):2459–2464 (1990).

Maisonpierre, Peter C. et al., "Human and Rat BrainDerived Neurotrophic Factor and Neurotrophin–3: Gene Structures, Distributions, and Chromosomal Localizations," *Genomics*, 10:558–568 (1991).

*Primary Examiner*—Gary L. Kunz
*Assistant Examiner*—Pamela Holbrook
(74) *Attorney, Agent, or Firm*—Hamilton, Brook, Smith & Reynolds, P.C.

(57) ABSTRACT

Methods for diagnosing and treating neuropsychiatric disorders, especially bipolar disorder, and to methods for identifying compounds for use in the diagnosis and treatment of neuropsychiatric disorders are disclosed. Also disclosed are novel compounds and pharmaceutical compositions for use in the diagnosis and treatment of neuropsychiatric disorders such as bipolar disorder.

6 Claims, 16 Drawing Sheets

```
SEQ ID
 1      hB(G) 1 ATTAAAC CACATACAGCACACTACTGA CACTGATTTGTGTCTGGTGC AG→
 2      hB(C) 1 ........ ...................... .................... ..
 3      rB(G) 1
 4      rB(C)
 5      mB(C) 1
 6      pB(C) 1                                                                        AAACCGGG

→hB(G) CTGCAGTTTATCACTAAG ACATAAAAAAACTTTGACCC TGCAGAATGGCCTGGAATTA CAATCAGATGGGCCACATG→
      hB(C) .................. .................... .................... ..................
      rB(G)                       AAAAA.GAA A.A.A..A..T...A..... ...G..............-.
      rB(C)
      mB(C)
      pB(C) CACCAAAGATTCCCCCCT ACCGCTTCTTTTTGACCAAA GGGAACGTGAAAAAATAATA GAGTCTGGGGATTTCGGGG

SPLICE
                                           Pro Val Phe Cys Leu Val Ser Ala Phe Ser Leu Gln
 7  →hB(G)  G CATCCCGGTGAAAGAAAGCCC TAA CCA GTT TTC TGT CTT GTT TCT GCT TTC TCC CTA CAG →
      hB(C)  . ..................... ... ... ... ... ... ... ... ... ... ... ... ... ...
      rB(G)  . TG....CAA..... T___ .GT. ... ..T ... C.G ... ... .C. ... .C. .T. .C. ...
      rB(C)         CGGCCTTGGACAG AGC CAG CGG ATT TGT CCG AGG TGG TAG TAC TTC ATC ...
      mB(C)         GTCTTCCCCAGAGCAGC TGC CTT GAT GTT TAC TTT GAC AAG TAG TGA CTG AAA A...
      pB(C)  C CGAAGTCTTCCCAGAGCAGC TGC CTT GAT GTT TAC TTT GAC AAG TAG TGA CTG AAA A...

?SPLICE2|                   |>>>START "B">>>
            Phe His Gln|Val Arg Arg Val|MET Thr Ile Leu Phe Leu
    →hB(C)206 TTC CAC CAG|GTG AGA AGA GTG|ATG ACC ATC CTT TTC CTT →
      rB(C) 52 ... ... ...|... ... ... ...|... ... ... ... ... ...
      mB(C) 57 ... ... ...|... ... ... ...|... ... ... ... ... ...
      pB(C)147 ... ... ...|... ... ... ...|... ... ... ... ... ...

-120                                        -110
         Thr Met Val Ile Ser Tyr Phe Gly Cys Met Lys Ala Ala Pro Met Lys Glu Ala Asn Ile
    →hB(C) ACT ATG GTT ATT TCA TAC TTT GGT TGC ATG AAG GCT GCC CCC ATG AAA GAA GCA AAC ATC→
                                                                                       Val
 8    rB(C) ... ... ... ... ... ... ..C ... ... ... ..G ... ... ... ... ... ... ... G..
                                                                                   Val Val
 9    mB(C) ... ... ... ... ... ... ..C ... ..A ... ..G ... ... ... ... ..T. ... G..
                                                                                       Val
10    pB(C) ... ... ... ... ... ... ..C ... .... ... ... ... ... ... ... ... ..C ... G..

-100                                          -90
         Arg Gly Gln Gly Gly Leu Ala Tyr Pro Gly Val Arg Thr His Gly Thr Leu Glu Ser
    →hB(C) CGA GGA CAA GGT GGC TTG GCC TAC CCA GGT GTG CGG ACC CAT GGG ACT CTG GAG AGC→
         His         Asn                 Ala
      rB(C) .AC ... ... ..C AA. ... ... ... ... .C. ... ... ... ... ... ... ... ...
         His         Asn
      mB(C) .AC ... ... ..C AA. ... ... ... ... ... ... ... ... ... ... ... ... ...
                     Ser
      pB(C) ... ... ... ..C A.. ... ... ... ... ... ... ... ... ... ... ... ... ...

-80
         Val Asn Gly Pro Lys Ala Gly Ser Arg Gly Leu Thr ---
    →hB(C)364 GTG AAT GGG CCC AAG GCA GGT TCA AGA GGC TTG ACA --- →
                                             Arg                 Thr
      rB(C)208 ... ... ... ... ... ... .G. ... ..G ... ..T C.. ..G ACG
                                             Arg                 Thr
      mB(C)213 ... ... ... ... ... ... .G. ... ..G ... ..T C... ..G ACG
                                                                     Ser
      pB(C)303 ... ... ... ... ... ... ... ... ... ... ... C..... TCG

-70                                      -60
         --- --- --- --- Ser Leu Ala Asp Thr Phe Glu His Val Ile Glu Glu Leu Leu Asp Glu
    →hB(C) --- --- --- --- TCA TTG GCT GAC ACT TTC GAA CAC GTG ATA GAA GAG CTG TTG GAT GAG→
         Thr
      rB(C) ACG --- --- --- ..C C.. ... ... ... ..T ..G ... ..C ... ... ... C... ... ...
         Thr
      mB(C) ACA --- --- --- ... C.. ... ... ..T ..G ... ..C ..C ... ... ... C... ... ...
         Ser Ser Ser Ser
      pB(C) TCG TCA TCG TCG ..G ... ..G ... ... ..T ... ... .C. ..G ... ... ... ... ..C ...
```

Fig. 1A

```
                        -50                                                              -40
         Asp Gln Lys Val Arg Pro Asn Glu Glu Asn Asn Lys Asp Ala Asp Leu Tyr Thr Ser
→hB(C)   GAC CAG AAA GTT CGG CCC AAT GAA GAA AAC AAT AAG GAC GCA GAC TTG TAC ACG TCC →
                                                            His
 rB(C)   ... ... ..G ... ... ... ... ..C ... ... ... ... C.. ... ... ..G ... ... ..T ...
                                                            His
 mB(C)   ... ... ..G ... ... ... ... ..C ... ... ... ..C C.T ... ..G ... ... ... ..T ...
                                                                         Met
 pB(C)   ... ... ... ... ... ... ... ..G ... ... ... ... ... ..G ... A.. ..T ... ...

-30
         Arg Val Met Leu Ser Ser Gln Val Pro Leu Glu Pro Pro
→hB(C)505 AGG GTG ATG CTC AGT AGT CAA GTG CCT TTG GAG CCT CCT →
 rB(C)355 C.. ... ... ... ..C ... ... ... ... ... ... ... ...
 mB(C)360 C.. ... ... ... ..C ... ... ... ... ... ... ... ...
 pB(C)459 C.A ..C ... ... ..C ... ... ... ... ... ... ... ...

-20                                          -10              GLYCOS.
         Leu Leu Phe Leu Leu Glu Glu Tyr Lys Asn Tyr Leu Asp Ala Ala Asn Met Ser Met Arg
→hB(C)   CTT CTC TTT CTG CTG GAG GAA TAC AAA AAT TAC CTA GAT GCT GCA AAC ATG TCC ATG AGG →
 rB(C)   ..G ... ... ... ... ... ... ... ... ... ... ..G ... ..C ... ... ... ..T ... ...
 mB(C)   ... ..A ... ... ... ... ... ... ... ... ... ..G ... ... ... ... ... ..T ... ...
 pB(C)   ... ... ... ... ... ... ... ... ... ... ... ..G ... ... ... ... ... ... ... ...

CLEAVE -1| +1 >>>MATURE>>>                                    +10
               Val Arg Arg|His Ser Asp Pro Ala Arg Arg Gly Glu Leu Ser Val CYS Asp Ser Ile
→hB(C)         GTC CGG CGC|CAC TCT GAC CCT GCC CGC CGA GGG GAG CTG AGC GTG TGT GAC AGT ATT →
 rB(C)         ..T ... ...|... ..C ... ..C ... ... ..T ... ... ... ... ... ... ... ... ...
 mB(C)         ... ... ...|... ..G ... ... ... ..G ... ... ... ... ... ... ... ... ... ...
 pB(C)         ... ... ...|... ..G ... ..G ... ... ..C ... ... ... ... ..C ... ... ..C ...

+20
         Ser Glu Trp Val Thr Ala Ala Asp Lys Lys Thr Ala Val
→hB(C)661 AGT GAG TGG GTA ACG GCG GCA GAC AAA AAG ACT GCA GTG →
 rB(C)511 ..C ... ... ... ..C ..A ... ... ..T ... ... ... ...
 mB(C)516 ..C ... ... ... ..C ..A ... ... ..T ... ... ... ...
 pB(C)615 ..C ... ... ... ..G ... ... ..G ..T ... ... ..G ...

+30                                          +40
         Asp Met Ser Gly Gly Thr Val Thr Val Leu Glu Lys Val Pro Val Ser Lys Gly Gln Leu
→hB(C)   GAC ATG TCG GGC GGG ACG GTC ACA GTC CTT GAA AAG GTC CCT GTA TCA AAA GGC CAA CTG →
 rB(C)   ... ... ..C ..T ... ... ... ... ... ..G ..G ..A ... ..G ... ... ... ... ... ...
 mB(C)   ... ... ... ..T ... ... ... ... ... ..A ..G ..A ... ..G ... ... ..C ... ... ...
 pB(C)   ... ... ... ..T ..C ... ... ... ..G ... ..C ... ..A ... ..C ..C ..G ... ... ...

+50                                          +60
         Lys Gln Tyr Phe Tyr Glu Thr Lys CYS Asn Pro Met Gly Tyr Thr Lys Glu Gly CYS
→hB(C)   AAG CAA TAC TTC TAC GAG ACC AAG TGC AAT CCC ATG GGT TAC ACA AAA GAA GGC TGC →
 rB(C)   ... ... ..T ... ... ... ... ..T ... ... ... ... ... ... ... ..G ..G ... ...
 mB(C)   ... ..G ..T ... ... ... ... ..T ... ... ... ... ... ... ... ..C ..G ... ...
 pB(C)   ... ..G ... ... ... ... ... ... ... ... ... ..T ... ..G ... ... ..G ..G ...

+70                                           +80
         Arg Gly Ile Asp Lys Arg His Trp Asn Ser Gln CYS Arg
→hB(C)817 AGG GGC ATA GAC AAA AGG CAT TGG AAC TCC CAG TGC CGA →
 rB(C)667 ... ... ... ... ... ..C ... ... ..G ..A ... ... ...
 mB(C)672 ... ... ... ... ... ..C ... ... ..G ..A ... ... ...
 pB(C)771 ... ... ... ..G ... ..C ... ... ... ... ... ... ...

+90                                           +100
         Thr Thr Gln Ser Tyr Val Arg Ala Leu Thr Met Asp Ser Lys Lys Arg Ile Gly Trp Arg
→hB(C)   ACT ACC CAG TCG TAC GTG CGG GCC CTT ACC ATG GAT AGC AAA AAG AGA ATT GGC TGG CGA →
 rB(C)   ... ... ..A ... ..T ... ... ... ... ..T ... ... ... ... ... ... ... ... ... ..G
 mB(C)   ... ... ..A ... ..T ..T ... ... ... ..T ... ... ... ... ... ... ... ... ... ...
 pB(C)   ... ... ... ... ..T ... ... ... ..C ... ... ... ... ... ... ..A C.. ... ... ..G

+110                                              +119
         Phe Ile Arg Ile Asp Thr Ser CYS Val CYS Thr Leu Thr Ile Lys Arg Gly Arg
→hB(C)   TTC ATA AGG ATA GAC ACT TCT TGT GTA TGT ACA TTG ACC ATT AAA AGG GGA AGA TAG
 rB(C)   ... ... ... ... ... ... ..C ... ... ... ..C ... ... ... ... ... ... ...
 mB(C)   ... ... ... ... ... ... ..C ... ... ... ..C ... ... ... ... ... ... ...
 pB(C)   ... ... ... ... ... ... ..C ... ... ... ..T ... ... ... ... ..G ... ...
```

Fig. 1B

| Fam | Individual | FID | MID | Sex | BONFU1 | REF | VAR |
|---|---|---|---|---|---|---|---|
| 3 | 003-001 | 3008 | 3007 | F | A-FAIL | | |
| 3 | 003-007 | 0 | 0 | F | REF | | |
| 3 | 003-008 | 0 | 0 | M | REF | | |
| 9 | 009-001 | 9007 | 9006 | M | REF | | |
| 9 | 009-005 | 9007 | 9006 | M | REF | | |
| 9 | 009-006 | 0 | 0 | F | HET | 2 | 0 |
| 9 | 009-007 | 0 | 0 | M | REF | | |
| 11 | 011-002 | 11005 | 11006 | F | HET | | |
| 11 | 011-005 | 0 | 0 | M | REF | | |
| 11 | 011-006 | 0 | 0 | F | HET | 0 | 2 |
| 11 | 011-001 | 11005 | 11006 | F | HET | | |
| 12 | 012-001 | 12006 | 12005 | M | REF | | |
| 12 | 012-003 | 12006 | 12005 | M | REF | | |
| 12 | 012-005 | 0 | 0 | F | REF | | |
| 12 | 012-006 | 0 | 0 | M | REF | | |
| 14 | 014-002 | 14006 | 14004 | F | REF | | |
| 14 | 014-004 | 0 | 0 | F | REF | | |
| 14 | 014-006 | 0 | 0 | M | HET | 1 | 1 |
| 14 | 014-001 | 14006 | 14004 | M | HET | | |
| 15 | 015-001 | 15010 | 15011 | M | REF | | |
| 15 | 015-002 | 15010 | 15011 | F | REF | | |
| 15 | 015-010 | 0 | 0 | M | REF | | |
| 15 | 015-011 | 0 | 0 | F | REF | | |
| 22 | 022-005 | 22010 | 22007 | M | REF | | |
| 22 | 022-007 | 0 | 0 | F | REF | | |
| 22 | 022-010 | 0 | 0 | M | REF | | |
| 22 | 022-001 | 22010 | 22007 | M | REF | | |
| 24 | 024-001 | 24005 | 24006 | M | VAR | | |
| 24 | 024-002 | 24005 | 24006 | F | VAR | | |
| 24 | 024-005 | 0 | 0 | M | HET | 0 | 2 |
| 24 | 024-006 | 0 | 0 | F | VAR | | |
| 27 | 027-003 | 27005 | 27008 | M | REF | | |
| 27 | 027-005 | 0 | 0 | M | REF | | |
| 27 | 027-008 | 0 | 0 | F | REF | | |

Fig. 2A

| Fam | Individual | FID | MID | Sex | BONFU1 | REF | VAR |
|---|---|---|---|---|---|---|---|
| 27 | 027-001 | 27005 | 27008 | M | REF | | |
| 30 | 030-001 | 30007 | 30008 | M | REF | | |
| 30 | 030-002 | 30007 | 30008 | F | REF | | |
| 30 | 030-007 | 0 | 0 | M | REF | | |
| 30 | 030-008 | 0 | 0 | F | REF | | |
| 39 | 039-012 | 0 | 0 | M | HET | 2 | 0 |
| 39 | 039-026 | 39012 | 39004 | M | HET | | |
| 39 | 039-027 | 39012 | 39004 | F | HET | | |
| 39 | 039-004 | 0 | 0 | F | VAR | | |
| 45 | 045-003 | 45006 | 45007 | M | HET | | |
| 45 | 045-004 | 45006 | 45007 | M | REF | | |
| 45 | 045-006 | 0 | 0 | M | HET | 1 | 1 |
| 45 | 045-007 | 0 | 0 | F | REF | | |
| 57 | 057-002 | 0 | 0 | F | REF | | |
| 57 | 057-004 | 57001 | 57002 | F | HET | | |
| 57 | 057-001 | 0 | 0 | M | HET | 0 | 1 |
| 58 | 058-001 | 58010 | 58011 | M | HET | | |
| 58 | 058-004 | 58010 | 58011 | M | HET | | |
| 58 | 058-010 | 0 | 0 | M | HET | 1 | 1 |
| 58 | 058-011 | 0 | 0 | F | HET | 1 | 1 |
| 61 | 061-014 | 0 | 0 | M | REF | | |
| 61 | 061-015 | 0 | 0 | F | HET | 2 | 0 |
| 61 | 061-001 | 61014 | 61015 | F | HET | | |
| 61 | 061-007 | 61014 | 61015 | F | HET | | |
| 63 | 063-001 | 63010 | 63011 | F | HET | | |
| 63 | 063-003 | 63010 | 63011 | M | HET | | |
| 63 | 063-010 | 0 | 0 | M | REF | | |
| 63 | 063-011 | 0 | 0 | F | HET | 0 | 2 |
| 64 | 064-026 | 0 | 0 | M | REF | | |
| 64 | 064-027 | 0 | 0 | F | REF | | |
| 64 | 064-001 | 64026 | 64027 | F | REF | | |
| 64 | 064-002 | 64026 | 64027 | M | REF | | |
| 65 | 065-001 | 0 | 0 | M | REF | | |

Fig. 2B

| Fam | Individual | FID | MID | Sex | BONFU1 | REF | VAR |
|---:|---|---:|---:|---|---|---|---|
| 65 | 065-006 | 0 | 0 | F | REF | | |
| 65 | 065-014 | 65001 | 65006 | M | REF | | |
| 65 | 065-015 | 65001 | 65006 | M | REF | | |
| 74 | 074-014 | 0 | 0 | M | HET | 2 | 0 |
| 74 | 074-015 | 0 | 0 | F | REF | | |
| 74 | 074-001 | 74014 | 74015 | F | REF | | |
| 74 | 074-005 | 74014 | 74015 | F | HET | | |
| 75 | 075-001 | 75005 | 75006 | M | REF | | |
| 75 | 075-002 | 75005 | 75006 | M | REF | | |
| 75 | 075-005 | 0 | 0 | M | HET | 2 | 0 |
| 75 | 075-006 | 0 | 0 | F | REF | | |
| 79 | 079-011 | 0 | 0 | M | HET | 1 | 1 |
| 79 | 079-013 | 0 | 0 | F | REF | | |
| 79 | 079-001 | 79011 | 79013 | F | HET | | |
| 79 | 079-002 | 79011 | 79013 | F | REF | | |
| 84 | 084-006 | 84011 | 84012 | F | REF | | |
| 84 | 084-011 | 0 | 0 | M | REF | | |
| 84 | 084-012 | 0 | 0 | F | REF | | |
| 87 | 087-001 | 87006 | 87005 | F | REF | | |
| 87 | 087-005 | 0 | 0 | F | REF | | |
| 87 | 087-006 | 0 | 0 | M | REF | | |
| 92 | 092-001 | 92004 | 92005 | F | REF | | |
| 92 | 092-004 | 0 | 0 | M | REF | | |
| 92 | 092-005 | 0 | 0 | F | REF | | |
| 93 | 093-001 | 93015 | 93016 | F | REF | | |
| 93 | 093-015 | 0 | 0 | M | HET | 1 | 0 |
| 93 | 093-016 | 0 | 0 | F | HET | 1 | 0 |
| 94 | 094-001 | 94004 | 94005 | F | REF | | |
| 94 | 094-004 | 0 | 0 | M | REF | | |
| 94 | 094-005 | 0 | 0 | F | REF | | |
| 95 | 095-001 | 95012 | 95013 | F | REF | | |
| 95 | 095-007 | 95012 | 95013 | M | REF | | |
| 95 | 095-013 | 0 | 0 | F | FAIL | | |

Fig. 2C

| Fam | Individual | FID | MID | Sex | BONFU1 | REF | VAR |
|---|---|---|---|---|---|---|---|
| 97 | 097-001 | 97012 | 97013 | F | HET | | |
| 97 | 097-012 | 0 | 0 | M | REF | | |
| 97 | 097-013 | 0 | 0 | F | VAR | | |
| 100 | 100-001 | 100014 | 100015 | F | REF | | |
| 100 | 100-005 | 100014 | 100015 | F | REF | | |
| 100 | 100-014 | 0 | 0 | M | REF | | |
| 100 | 100-015 | 0 | 0 | F | HET | 2 | 0 |
| 108 | 108-011 | 0 | 0 | M | HET | 1 | 0 |
| 108 | 108-020 | 0 | 0 | F | REF | | |
| 108 | 108-001 | 108011 | 108020 | F | REF | | |
| 109 | 109-001 | 109015 | 109017 | F | REF | | |
| 109 | 109-004 | 109015 | 109017 | F | REF | | |
| 109 | 109-015 | 0 | 0 | M | REF | | |
| 109 | 109-017 | 0 | 0 | F | REF | | |
| 111 | 111-004 | 0 | 0 | M | REF | | |
| 111 | 111-008 | 0 | 0 | F | HET | 1 | 1 |
| 111 | 111-001 | 111004 | 111008 | F | HET | | |
| 111 | 111-002 | 111004 | 111008 | F | REF | | |
| 112 | 112-001 | 112012 | 112008 | F | REF | | |
| 112 | 112-004 | 112012 | 112008 | F | REF | | |
| 112 | 112-008 | 0 | 0 | F | REF | | |
| 113 | 113-018 | 0 | 0 | F | REF | | |
| 113 | 113-001 | 113005 | 113018 | M | REF | | |
| 113 | 113-002 | 113005 | 113018 | M | REF | | |
| 113 | 113-005 | 0 | 0 | M | REF | | |
| 114 | 114-001 | 114005 | 114010 | M | VAR | | |
| 114 | 114-003 | 114005 | 114010 | M | HET | | |
| 114 | 114-010 | 0 | 0 | F | HET | 0 | 1 |
| 115 | 115-001 | 115007 | 115011 | F | HET | | |
| 115 | 115-004 | 115007 | 115011 | F | HET | | |
| 115 | 115-007 | 0 | 0 | M | HET | 1 | 1 |

Fig. 2D

| Fam | Individual | FID | MID | Sex | BONFU1 | REF | VAR |
|---|---|---|---|---|---|---|---|
| 115 | 115-011 | 0 | 0 | F | HET | 1 | 1 |
| 116 | 116-001 | 116007 | 116008 | F | A-FAIL | | |
| 116 | 116-004 | 116007 | 116008 | M | FAIL | | |
| 116 | 116-007 | 0 | 0 | M | REF | | |
| 116 | 116-008 | 0 | 0 | F | HET | 1 | 0 |
| 117 | 117-001 | 117006 | 117007 | M | REF | | |
| 117 | 117-005 | 117006 | 117007 | F | REF | | |
| 117 | 117-007 | 0 | 0 | F | HET | 2 | 0 |
| 118 | 118-002 | 118005 | 118010 | F | HET | | |
| 118 | 118-005 | 0 | 0 | M | REF | | |
| 118 | 118-010 | 0 | 0 | F | HET | 1 | 1 |
| 118 | 118-001 | 118005 | 118010 | F | REF | | |
| 121 | 121-001 | 121008 | 121009 | F | REF | | |
| 121 | 121-002 | 121008 | 121009 | M | REF | | |
| 121 | 121-008 | 0 | 0 | M | REF | | |
| 121 | 121-009 | 0 | 0 | F | REF | | |

Fig. 2E

| Fam | Individual | FID | MID | Sex | BONFU1 | REF | VAR |
|---|---|---|---|---|---|---|---|
| 122 | 122-002 | 122005 | 122006 | F | REF | | |
| 122 | 122-005 | 0 | 0 | M | HET | 2 | 0 |
| 122 | 122-006 | 0 | 0 | F | HET | 1 | 1 |
| 122 | 122-001 | 122005 | 122006 | M | HET | | |
| 123 | 123-001 | 123007 | 123014 | F | REF | | |
| 123 | 123-004 | 123007 | 123014 | F | REF | | |
| 123 | 123-007 | 0 | 0 | M | REF | | |
| 123 | 123-014 | 0 | 0 | F | REF | | |
| 124 | 124-034 | 0 | 0 | M | HET | 1 | 1 |
| 124 | 124-035 | 124034 | 124001 | M | REF | | |
| 124 | 124-036 | 124034 | 124001 | M | HET | | |
| 124 | 124-001 | 0 | 0 | F | REF | | |
| 125 | 125-001 | 0 | 0 | | REF | | |
| 125 | 125-005 | 0 | 0 | | HET | 1 | 0 |
| 125 | 125-012 | 0 | 0 | | REF | | |
| 128 | 128-014 | 0 | 0 | F | REF | | |
| 128 | 128-001 | 128006 | 128014 | F | REF | | |
| 128 | 128-002 | 128006 | 128014 | F | REF | | |
| 132 | 132-001 | 132006 | 132007 | M | HET | | |
| 132 | 132-005 | 132006 | 132007 | F | REF | | |
| 132 | 132-006 | 0 | 0 | M | REF | | |
| 132 | 132-007 | 0 | 0 | F | HET | 1 | 1 |
| 200 | 200-001 | 200008 | 200009 | M | HET | | |
| 200 | 200-008 | 0 | 0 | M | VAR | | |
| 200 | 200-009 | 0 | 0 | F | REF | | |
| 202 | 202-001 | 202007 | 202008 | F | REF | | |
| 202 | 202-007 | 0 | 0 | M | REF | | |
| 202 | 202-008 | 0 | 0 | F | REF | | |
| 203 | 203-001 | 203004 | 203005 | M | REF | | |
| 203 | 203-002 | 203004 | 203005 | F | HET | | |
| 203 | 203-004 | 0 | 0 | M | HET | 1 | 1 |
| 203 | 203-005 | 0 | 0 | F | HET | 2 | 0 |
| 204 | 204-006 | 0 | 0 | M | REF | | |

Fig. 2F

| Fam | Individual | FID | MID | Sex | BONFU1 | REF | VAR |
|---|---|---|---|---|---|---|---|
| 204 | 204-007 | 0 | 0 | F | REF | | |
| 204 | 204-001 | 204006 | 204007 | F | REF | | |
| 206 | 206-001 | 206011 | 206006 | M | REF | | |
| 206 | 206-006 | 0 | 0 | F | REF | | |
| 206 | 206-011 | 0 | 0 | M | REF | | |
| 210 | 210-001 | 210008 | 210009 | M | HET | | |
| 210 | 210-008 | 0 | 0 | M | REF | | |
| 210 | 210-009 | 0 | 0 | F | VAR | | |
| 211 | 211-001 | 211004 | 211005 | F | HET | | |
| 211 | 211-004 | 0 | 0 | M | HET | 1 | 0 |
| 211 | 211-005 | 0 | 0 | F | HET | 0 | 1 |
| 217 | 217-002 | 217005 | 217006 | M | HET | | |
| 217 | 217-005 | 0 | 0 | M | HET | 1 | 1 |
| 217 | 217-006 | 0 | 0 | F | HET | 2 | 0 |
| 217 | 217-001 | 217005 | 217006 | F | REF | | |
| 228 | 228-001 | 228004 | 228005 | F | HET | | |
| 228 | 228-004 | 0 | 0 | M | HET | 1 | 0 |
| 228 | 228-005 | 0 | 0 | F | VAR | | |
| 229 | 229-006 | 0 | 0 | F | REF | | |
| 229 | 229-001 | 229005 | 229006 | F | REF | | |
| 229 | 229-005 | 0 | 0 | M | REF | | |
| 231 | 231-001 | 231008 | 231009 | F | HET | | |
| 231 | 231-002 | 231008 | 231009 | F | HET | | |
| 231 | 231-008 | 0 | 0 | M | HET | 1 | 1 |
| 231 | 231-009 | 0 | 0 | F | HET | 1 | 1 |
| 233 | 233-008 | 0 | 0 | F | REF | | |
| 233 | 233-001 | 233007 | 233008 | F | REF | | |
| 233 | 233-002 | 233007 | 233008 | M | REF | | |
| 233 | 233-007 | 0 | 0 | M | HET | 2 | 0 |
| 236 | 236-001 | 236014 | 236015 | F | REF | | |
| 236 | 236-002 | 236014 | 236015 | M | REF | | |
| 236 | 236-014 | 0 | 0 | M | REF | | |
| 236 | 236-015 | 0 | 0 | F | REF | | |

Fig. 2G

| Fam | Individual | FID | MID | Sex | BONFU1 | REF | VAR |
|---|---|---|---|---|---|---|---|
| 239 | 239-007 | 0 | 0 | F | REF | | |
| 239 | 239-001 | 239006 | 239007 | M | REF | | |
| 239 | 239-005 | 239006 | 239007 | F | HET | | |
| 239 | 239-006 | 0 | 0 | M | HET | 1 | 1 |
| 240 | 240-001 | 240005 | 240006 | F | HET | | |
| 240 | 240-002 | 240005 | 240006 | F | HET | | |
| 240 | 240-005 | 0 | 0 | M | VAR | | |
| 240 | 240-006 | 0 | 0 | F | REF | | |
| 251 | 251-011 | 0 | 0 | F | REF | | |
| 251 | 251-001 | 251010 | 251011 | M | REF | | |
| 251 | 251-008 | 251010 | 251011 | M | REF | | |
| 251 | 251-010 | 0 | 0 | M | REF | | |
| 252 | 252-001 | 252008 | 252009 | F | HET | | |
| 252 | 252-005 | 252008 | 252009 | F | REF | | |
| 252 | 252-009 | 0 | 0 | F | HET | 1 | 0 |
| 257 | 257-001 | 257003 | 257004 | F | REF | | |
| 257 | 257-002 | 257003 | 257004 | M | REF | | |
| 257 | 257-003 | 0 | 0 | M | REF | | |
| 257 | 257-004 | 0 | 0 | F | REF | | |
| 260 | 260-001 | 260007 | 260008 | F | REF | | |
| 260 | 260-002 | 260007 | 260008 | F | REF | | |
| 260 | 260-007 | 0 | 0 | M | REF | | |
| 260 | 260-008 | 0 | 0 | F | REF | | |
| 263 | 263-001 | 263005 | 263006 | F | REF | | |
| 263 | 263-003 | 263005 | 263006 | F | REF | | |
| 263 | 263-005 | 0 | 0 | M | REF | | |
| 263 | 263-006 | 0 | 0 | F | REF | | |
| 266 | 266-001 | 266010 | 266011 | F | REF | | |
| 266 | 266-004 | 266010 | 266011 | F | REF | | |
| 266 | 266-010 | 0 | 0 | M | HET | 2 | 0 |
| 266 | 266-011 | 0 | 0 | F | REF | | |
| 267 | 267-001 | 267004 | 267005 | F | REF | | |

Fig. 2H

| Fam | Individual | FID | MID | Sex | BONFU1 | REF | VAR |
|---|---|---|---|---|---|---|---|
| 267 | 267-003 | 267004 | 267005 | M | REF | | |
| 267 | 267-004 | 0 | 0 | M | REF | | |
| 267 | 267-005 | 0 | 0 | F | REF | | |
| 300 | 300-001 | 300004 | 300005 | F | REF | | |
| 300 | 300-004 | 0 | 0 | M | HET | 1 | 0 |
| 300 | 300-005 | 0 | 0 | F | REF | | |
| 301 | 301-001 | 301012 | 301013 | F | HET | | |
| 301 | 301-008 | 301012 | 301013 | M | REF | | |
| 301 | 301-012 | 0 | 0 | M | HET | 1 | 1 |
| 301 | 301-013 | 0 | 0 | F | REF | | |
| 302 | 302-002 | 302009 | 302010 | F | HET | | |
| 302 | 302-009 | 0 | 0 | M | REF | | |
| 302 | 302-010 | 0 | 0 | F | HET | 1 | 1 |
| 302 | 302-001 | 302009 | 302010 | F | REF | | |
| 303 | 303-001 | 303009 | 303010 | M | REF | | |
| 303 | 303-006 | 303009 | 303010 | F | REF | | |
| 303 | 303-009 | 0 | 0 | M | REF | | |
| 303 | 303-010 | 0 | 0 | F | REF | | |
| 304 | 304-004 | 304008 | 304009 | F | HET | | |
| 304 | 304-008 | 0 | 0 | M | HET | 0 | 2 |
| 304 | 304-009 | 0 | 0 | F | REF | | |
| 304 | 304-001 | 304008 | 304009 | M | HET | | |
| 305 | 305-001 | 305010 | 305011 | M | REF | | |
| 305 | 305-002 | 305010 | 305011 | F | REF | | |
| 305 | 305-010 | 0 | 0 | M | HET | 2 | 0 |
| 305 | 305-011 | 0 | 0 | F | REF | | |
| 308 | 308-003 | 0 | 0 | M | REF | | |
| 308 | 308-004 | 0 | 0 | F | VAR | | |
| 308 | 308-001 | 308003 | 308004 | F | HET | | |
| 403 | 403-001 | 403004 | 403005 | F | REF | | |
| 403 | 403-004 | 0 | 0 | M | REF | | |
| 403 | 403-005 | 0 | 0 | F | REF | | |
| | | | | | REF | | |

Fig. 21

| Fam | Individual | FID | MID | Sex | BONFU1 | REF | VAR |
|-----|------------|-----|-----|-----|--------|-----|-----|
|     |            |     |     |     | HET    |     |     |
|     |            |     |     |     | VAR    |     |     |
|     |            |     |     |     | NTC    |     |     |
|     |            |     |     |     | REF    |     |     |
|     |            |     |     |     | HET    |     |     |
|     |            |     |     |     | VAR    |     |     |
|     |            |     |     |     | NTC    |     |     |
|     |            |     |     |     | HET    |     |     |
|     |            |     |     |     | VAR    |     |     |
|     |            |     |     |     | NTC    |     |     |
|     |            |     |     |     |        | 54  | 30  |
|     |            |     |     |     |        |     |     |
|     |            |     |     |     | 585714 |     |     |
|     |            |     |     |     | 001766 |     |     |

Fig. 2J

| Fam | Individual | Status | SBEFRET | GeREF | VAR |
|---|---|---|---|---|---|
| 401 | 401-001 | parent | A-FAIL | | |
| 401 | 401-005 | parent | REF | | |
| 401 | 401-006 | parent | REF | | |
| 403 | 403-001 | parent | REF | | |
| 403 | 403-004 | parent | REF | | |
| 403 | 403-005 | parent | REF | | |
| 404 | 404-007 | parent | HET | 1 | 0 |
| 404 | 404-001 | parent | REF | | |
| 404 | 404-006 | parent | REF | | |
| 407 | 407-001 | parent | HET | | |
| 407 | 407-004 | parent | HET | 0 | 1 |
| 407 | 407-005 | parent | REF | | |
| 408 | 408-001 | parent | REF | | |
| 408 | 408-008 | parent | HET | 1 | 0 |
| 408 | 408-009 | parent | HET | 1 | 0 |
| 409 | 409-003 | parent | REF | | |
| 409 | 409-004 | parent | HET | 1 | 0 |
| 409 | 409-001 | parent | REF | | |
| 410 | 410-001 | parent | HET | | |
| 410 | 410-003 | parent | HET | 0 | 1 |
| 410 | 410-004 | parent | REF | | |
| 412 | 412-001 | parent | REF | | |
| 412 | 412-009 | parent | REF | | |
| 412 | 412-010 | parent | REF | | |
| 414 | 414-001 | parent | REF | | |
| 414 | 414-006 | parent | REF | | |
| 414 | 414-007 | parent | HET | 1 | 0 |
| 415 | 415-001 | parent | HET | | |
| 415 | 415-004 | parent | REF | | |
| 415 | 415-005 | parent | HET | 0 | 1 |
| 417 | 417-005 | parent | REF | | |
| 417 | 417-001 | parent | REF | | |
| 417 | 417-004 | parent | REF | | |

Fig. 3A

| Fam | Individual | Status | SBEFRET | GeREF | VAR |
|---|---|---|---|---|---|
| 421 | 421-001 | parent | VAR | | |
| 421 | 421-004 | parent | VAR | | |
| 421 | 421-005 | parent | VAR | | |
| 422 | 422-001 | parent | REF | | |
| 422 | 422-004 | parent | REF | | |
| 422 | 422-005 | parent | HET | 1 | 0 |
| 425 | 425-005 | parent | REF | | |
| 425 | 425-006 | parent | REF | | |
| 425 | 425-001 | parent | REF | | |
| 426 | 426-001 | parent | REF | | |
| 426 | 426-005 | parent | REF | | |
| 426 | 426-006 | parent | REF | | |
| 428 | 428-001 | parent | REF | | |
| 428 | 428-004 | parent | REF | | |
| 428 | 428-005 | parent | REF | | |
| 430 | 430-001 | parent | REF | | |
| 430 | 430-003 | parent | REF | | |
| 430 | 430-004 | parent | REF | | |
| 435 | 435-001 | parent | REF | | |
| 435 | 435-003 | parent | HET | 1 | 0 |
| 435 | 435-004 | parent | REF | | |
| 437 | 437-006 | parent | HET | 1 | 0 |
| 437 | 437-001 | parent | REF | | |
| 437 | 437-005 | parent | REF | | |
| 442 | 442-001 | parent | HET | | |
| 442 | 442-004 | parent | VAR | | |
| 442 | 442-005 | parent | REF | | |
| 444 | 444-008 | parent | REF | | |
| 444 | 444-009 | parent | HET | 0 | 1 |
| 444 | 444-010 | parent | HET | | |
| 447 | 447-004 | parent | REF | | |
| 447 | 447-005 | parent | HET | 1 | 0 |
| 447 | 447-001 | parent | REF | | |

Fig. 3B

| Fam | Individual | Status | SBEFRET | GeREF | VAR |
|---|---|---|---|---|---|
| 451 | 451-001 | parent | FAIL | | |
| 451 | 451-004 | parent | VAR | | |
| 451 | 451-005 | parent | HET | | |
| 458 | 458-001 | parent | REF | | |
| 458 | 458-006 | parent | HET | 1 | 0 |
| 458 | 458-007 | parent | REF | | |
| 461 | 461-001 | parent | REF | | |
| 461 | 461-004 | parent | REF | | |
| 461 | 461-005 | parent | REF | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | A-FAIL | | |
| | | | | 0 | 4 |

Fig. 3C

SEQUENCE LISTING

<160> NUMBER OF SEQ ID NOS: 13

<210> SEQ ID NO 1
<211> LENGTH: 187
<212> TYPE: DNA
<213> ORGANISM: Homo sapiens

<400> SEQUENCE: 1

| | | | | | |
|---|---|---|---|---|---|
| attaaaccac | atacagcaca | ctactgacac | tgatttgtgt | ctggtgcagc | tggagtttat | 60 |
| cactaagaca | taaaaaaacc | ttgaccctgc | agaatggcct | ggaattacaa | tcagatgggc | 120 |
| cacatggcat | cccggtgaaa | gaaagcccta | accagttttc | tgtcttgttt | ctgctttctc | 180 |
| cctacag | | | | | | 187 |

<210> SEQ ID NO 2
<211> LENGTH: 952
<212> TYPE: DNA
<213> ORGANISM: Homo sapiens

<400> SEQUENCE: 2

| | | | | | |
|---|---|---|---|---|---|
| attaaaccac | atacagcaca | ctactgacac | tgatttgtgt | ctggtgcagc | tggagtttat | 60 |
| cactaagaca | taaaaaaacc | ttgaccctgc | agaatggcct | ggaattacaa | tcagatgggc | 120 |
| cacatggcat | cccggtgaaa | gaaagcccta | accagttttc | tgtcttgttt | ctgctttctc | 180 |
| cctacagttc | caccaggtga | agagtgat | gaccatcctt | tccttacta | tggttatttc | 240 |
| atactttggt | tgcatgaagg | ctgcccccat | gaaagaagca | aacatccgag | gacaaggtgg | 300 |
| cttggcctac | ccaggtgtgc | ggacccatgg | gactctggag | agcgtgaatg | ggcccaaggc | 360 |
| aggttcaaga | ggcttgacat | cattggctga | cactttcgaa | cacgtgatag | aagagctgtt | 420 |
| ggatgaggac | cagaaagttc | ggcccaatga | agaaacaat | aaggacgcag | acttgtacac | 480 |
| gtccagggtg | atgctcagta | gtcaagtgcc | tttggagcct | cctcttctct | ttctgctgga | 540 |
| ggaatacaaa | aattacctag | atgctgcaaa | catgtccatg | agggtccggc | gccactctga | 600 |
| ccctgcccgc | cgaggggagc | tgagcgtgtg | tgacagtatt | agtgagtggg | taacggcggc | 660 |
| agacaaaaag | actgcagtgg | acatgtcggg | cgggacggtc | acagtccttg | aaaaggtccc | 720 |
| tgtatcaaaa | ggccaactga | agcaatactt | ctacgagacc | aagtgcaatc | ccatgggtta | 780 |
| cacaaaagaa | ggctgcaggg | gcatagacaa | aaggcattgg | aactcccagt | gccgaactac | 840 |
| ccagtcgtac | gtgcgggccc | ttaccatgga | tagcaaaaag | agaattggct | ggcgattcat | 900 |
| aaggatagac | acttcttgtg | tatgtacatt | gaccattaaa | agggaagat | ag | 952 |

<210> SEQ ID NO 3
<211> LENGTH: 136
<212> TYPE: DNA
<213> ORGANISM: Unknown
<220> FEATURE:
<223> OTHER INFORMATION: Rat

<400> SEQUENCE: 3

| | | | | | |
|---|---|---|---|---|---|
| ctggagttta | tcactaagac | ataaaaaaaa | aaaagaaag | aaaaaggac | tgaaattaca | 60 |
| agcagatggc | cacatggtgt | ccccaagaaa | gtaaggtcta | acctgttctg | tgtctgtctc | 120 |
| tgcttccttc | ccacag | | | | | 136 |

<210> SEQ ID NO 4
<211> LENGTH: 832

<212> TYPE: DNA
<213> ORGANISM: Unknown
<220> FEATURE:
<223> OTHER INFORMATION: Rat

<400> SEQUENCE: 4

| | | | | | |
|---|---|---|---|---|---|
| gcatcccggt | cgccttggac | agagccagcg | gatttgtccg | aggtggtagt | acttcatcca | 60 |
| gttccaccag | gtgagaagag | tgatgaccat | ccttttcctt | actatggtta | tttcatactt | 120 |
| cggttgcatg | aaggctgcgc | ccatgaaaga | agcaaacgtc | cacggacaag | gtaacttggc | 180 |
| ctacccagct | gtgcggaccc | atgggactct | ggagagcgtg | aatgggccca | gggcaggttc | 240 |
| gagaggtctg | acaacgacgt | ccctggctga | cacttttgag | cacgtgatcg | aagagctgct | 300 |
| ggatgaggac | cagaaggttc | ggcccaacga | agaaaaccat | aaggacgcgg | acttgtacac | 360 |
| ttcccgggtg | atgctcagca | gtcaagtgcc | tttggagcct | cctctgctct | ttctgctgga | 420 |
| ggaatacaaa | aattacctgg | atgccgcaaa | catgtctatg | agggttcggc | gccactccga | 480 |
| ccccgcccgc | cgtggggagc | tgagcgtgtg | tgacagtatt | agcgagtggg | tcacagcggc | 540 |
| agataaaaag | actgcagtgg | acatgtccgg | tgggacggtc | acagtcctgg | agaaagtccc | 600 |
| ggtatcaaaa | ggccaactga | agcaatattt | ctacgagacc | aagtgtaatc | ccatggggtta | 660 |
| cactaaggaa | ggctgcaggg | gcatagacaa | aaggcactgg | aactcgcaat | gccgaactac | 720 |
| ccaatcgtat | gttcgggccc | ttactatgga | tagcaaaaag | agaattggct | ggcggttcat | 780 |
| aaggatagac | acttcctgtg | tatgtacact | gaccattaaa | agggaagat | ag | 832 |

<210> SEQ ID NO 5
<211> LENGTH: 832
<212> TYPE: DNA
<213> ORGANISM: Unknown
<220> FEATURE:
<223> OTHER INFORMATION: Mouse

<400> SEQUENCE: 5

| | | | | | |
|---|---|---|---|---|---|
| gcatcgtctt | ccccagagca | gctgccttga | tgtttacttt | gacaagtagt | gactgaaaaa | 60 |
| gttccaccag | gtgagaagag | tgatgaccat | ccttttcctt | actatggtta | tttcatactt | 120 |
| cggttgcatg | aaagctgcgc | ccatgaaaga | agtaaacgtc | cacggacaag | gcaacttggc | 180 |
| ctacccaggt | gtgcggaccc | atgggactct | ggagagcgtg | aatgggccca | gggcaggttc | 240 |
| gagaggtctg | acgacgacat | cactggctga | cacttttgag | cacgtcatcg | aagagctgct | 300 |
| ggatgaggac | cagaaggttc | ggcccaacga | agaaaacaac | catgacgcgg | acttgtacac | 360 |
| ttcccgggtg | atgctcagca | gtcaagtgcc | tttggagcct | cctcttctat | ttctgctgga | 420 |
| ggaatacaaa | aattacctgg | atgctgcaaa | catgtctatg | agggtccggc | gccactcgga | 480 |
| ccctgcccgc | cggggggagc | tgagcgtgtg | tgacagtatt | agcgagtggg | tgacagcggc | 540 |
| agataaaaag | actgcagtgg | acatgtctgg | cgggacggtc | acagtcctag | agaaagtccc | 600 |
| ggtatcgaaa | ggccaactga | agcagtattt | ctacgagacc | aagtgtaatc | ccatggggtta | 660 |
| caccaaggaa | ggctgcaggg | gcatagacaa | aaggcattgg | aactcgcaat | gccgaactac | 720 |
| ccaatcgtat | gttcgggccc | ttactatgga | tagcaaaaag | agaattggct | ggcgattcat | 780 |
| aaggatagac | acttcctgtg | tatgtacact | gaccattaaa | agggaagat | ag | 832 |

<210> SEQ ID NO 6
<211> LENGTH: 926
<212> TYPE: DNA
<213> ORGANISM: Unknown
<220> FEATURE:

<223> OTHER INFORMATION: Pig

<400> SEQUENCE: 6

```
aaaccgggca ccaaagattc cccctaccc cttcttttg accaaaggga acgtgaaaaa    60
ataatagagt ctggggattt cggggccgaa gtcttcccca gagcagctgc cttgatgttt   120
actttgacaa gtagtgactg aaaaagttcc accaggtgag aagagtgatg accatccttt   180
tccttactat ggttatttca actttggtt gcatgaaggc tgcccccatg aaagaagcaa    240
acgtccgagg acaaggcagc ttggcctacc caggtgtgcg gacccatggg actctggaga   300
gcgtgaatgg gcccaaggca ggttcaagag gcctgacatc gtcgtcatcg tcgtcgttgg   360
cggacacttt tgaacacgtg atcgaggagc tgttggacga ggaccagaaa gttcggccca   420
atgaggaaaa caataaggac gcggacatgt atacgtcccg agtcatgctc agcagtcaag   480
tgcctttgga gcctcctctt ctctttctgc tggaggaata caaaaattac ctggatgctg   540
caaacatgtc catgagggtc cggcgccact cggacccggc ccgccgcggg gagctgagcg   600
tgtgcgacag cattagcgag tgggtgacgg cggcggataa aaagaccgca gtggacatgt   660
cgggtggcac ggtcacggtc ctcgaaaaag tccccgtctc gaaaggccaa ctgaagcagt   720
acttctacga gaccaagtgc aatcctatgg ggtacacaaa ggagggctgc aggggcatag   780
acaagaggca ctggaactcc cagtgccgaa ctacccagtc gtatgtgcgg gccctcacca   840
tggatagcaa aaacgaatt ggctggcgat tcataaggat agacacttcc tgtgtatgta   900
ctttgaccat taagaggga agatag                                         926
```

<210> SEQ ID NO 7
<211> LENGTH: 270
<212> TYPE: PRT
<213> ORGANISM: Homo sapiens

<400> SEQUENCE: 7

```
Pro Val Phe Cys Leu Val Ala Ser Ala Phe Ser Leu Gln Phe His Gln
  1               5                  10                  15
Val Ala Arg Gly Arg Val Met Thr Ile Leu Phe Leu Thr Met Val Ile
             20                  25                  30
Ser Tyr Phe Gly Cys Met Lys Ala Ala Pro Met Lys Glu Ala Asn Ile
         35                  40                  45
Arg Gly Gln Gly Gly Leu Ala Tyr Pro Gly Val Arg Thr His Gly Thr
     50                  55                  60
Leu Glu Ser Val Asn Gly Pro Lys Ala Gly Ser Arg Gly Leu Thr Ser
 65                  70                  75                  80
Leu Ala Asp Thr Phe Glu His Val Ala Ile Glu Glu Leu Leu Asp Glu
                 85                  90                  95
Asp Gln Lys Val Arg Pro Asn Glu Glu Asn Asn Lys Asp Ala Asp Leu
            100                 105                 110
Tyr Thr Ser Arg Val Met Leu Ser Ser Gln Val Pro Leu Glu Pro Pro
        115                 120                 125
Leu Leu Phe Leu Leu Glu Glu Tyr Lys Asn Tyr Leu Asp Ala Ala Asn
    130                 135                 140
Met Ser Met Arg Val Arg Arg His Ser Asp Pro Ala Arg Arg Gly Glu
145                 150                 155                 160
Leu Ser Val Cys Asp Ser Ile Ser Glu Trp Val Thr Ala Ala Asp Lys
                165                 170                 175
Lys Thr Ala Val Asp Met Ser Gly Gly Thr Val Thr Val Leu Glu Lys
            180                 185                 190
```

```
Val Pro Val Ser Lys Gly Gln Leu Lys Gln Tyr Phe Tyr Glu Thr Lys
        195                 200                 205

Cys Asn Pro Met Gly Tyr Thr Lys Glu Gly Cys Arg Gly Ile Asp Lys
        210                 215                 220

Arg His Trp Asn Ser Gln Cys Arg Thr Thr Gln Ser Tyr Val Arg Ala
225                 230                 235                 240

Leu Thr Met Asp Ser Lys Lys Arg Ile Gly Trp Arg Phe Ile Arg Ile
                245                 250                 255

Asp Thr Ser Cys Val Cys Thr Leu Thr Ile Lys Arg Gly Arg
        260                 265                 270

<210> SEQ ID NO 8
<211> LENGTH: 257
<212> TYPE: PRT
<213> ORGANISM: Unknown
<220> FEATURE:
<223> OTHER INFORMATION: Rat

<400> SEQUENCE: 8

Pro Val Phe Cys Leu Val Ala Ser Ala Phe Ser Leu Gln Thr Met Val
1               5                   10                  15

Ile Ser Tyr Phe Gly Cys Met Lys Ala Ala Pro Met Lys Glu Ala Asn
                20                  25                  30

Val His Gly Gln Gly Asn Leu Ala Tyr Pro Ala Val Arg Thr His Gly
            35                  40                  45

Thr Leu Glu Ser Val Asn Gly Pro Arg Ala Gly Ser Arg Gly Leu Thr
        50                  55                  60

Thr Thr Ser Leu Ala Asp Thr Phe Glu His Val Ala Ile Glu Glu Leu
65                  70                  75                  80

Leu Asp Glu Asp Gln Lys Val Arg Pro Asn Glu Glu Asn His Lys Asp
                85                  90                  95

Ala Asp Leu Tyr Thr Ser Arg Val Met Leu Ser Ser Gln Val Pro Leu
            100                 105                 110

Glu Pro Pro Leu Leu Phe Leu Leu Glu Glu Tyr Lys Asn Tyr Leu Asp
        115                 120                 125

Ala Ala Asn Met Ser Met Arg Val Arg Arg His Ser Asp Pro Ala Arg
    130                 135                 140

Arg Gly Glu Leu Ser Val Cys Asp Ser Ile Ser Glu Trp Val Thr Ala
145                 150                 155                 160

Ala Asp Lys Lys Thr Ala Val Asp Met Ser Gly Gly Thr Val Thr Val
                165                 170                 175

Leu Glu Lys Val Pro Val Ser Lys Gly Gln Leu Lys Gln Tyr Phe Tyr
            180                 185                 190

Glu Thr Lys Cys Asn Pro Met Gly Tyr Thr Lys Glu Gly Cys Arg Gly
        195                 200                 205

Ile Asp Lys Arg His Trp Asn Ser Gln Cys Arg Thr Thr Gln Ser Tyr
    210                 215                 220

Val Arg Ala Leu Thr Met Asp Ser Lys Lys Arg Ile Gly Trp Arg Phe
225                 230                 235                 240

Ile Arg Ile Asp Thr Ser Cys Val Cys Thr Leu Thr Ile Lys Arg Gly
                245                 250                 255

Arg

<210> SEQ ID NO 9
<211> LENGTH: 274
```

```
<212> TYPE: PRT
<213> ORGANISM: Unknown
<220> FEATURE:
<223> OTHER INFORMATION: Mouse

<400> SEQUENCE: 9

Pro Val Phe Cys Leu Val Ala Ser Ala Phe Ser Leu Gln Phe His Gln
 1               5                  10                  15

Val Ala Arg Gly Arg Val Met Thr Ile Leu Phe Leu Thr Met Val Ile
             20                  25                  30

Ser Tyr Phe Gly Cys Met Lys Ala Ala Pro Met Lys Glu Val Asn Val
             35                  40                  45

His Gly Gln Gly Asn Leu Ala Tyr Pro Gly Val Arg Thr His Gly Thr
     50                  55                  60

Leu Glu Ser Val Asn Gly Pro Arg Ala Gly Ser Arg Gly Leu Thr Thr
65                  70                  75                  80

Thr Ser Leu Ala Asp Thr Phe Glu His Val Ala Ile Glu Glu Leu Leu
             85                  90                  95

Asp Glu Asp Gln Lys Val Arg Pro Asn Glu Glu Asn Asn His Asp Ala
            100                 105                 110

Asp Leu Tyr Thr Ser Arg Val Met Leu Ser Ser Gln Val Pro Leu Glu
        115                 120                 125

Pro Pro Leu Leu Phe Leu Leu Glu Glu Tyr Lys Asn Tyr Leu Asp Ala
    130                 135                 140

Ala Asn Met Ser Met Arg Val Arg Arg His Ser Asp Pro Ala Arg Arg
145                 150                 155                 160

Gly Glu Leu Ser Val Cys Asp Ser Ile Ser Glu Trp Val Thr Ala Ala
                165                 170                 175

Asp Lys Lys Thr Ala Val Asp Met Ser Gly Thr Val Thr Val Leu
            180                 185                 190

Glu Lys Val Pro Val Ser Lys Gly Gln Leu Lys Gln Tyr Phe Tyr Glu
        195                 200                 205

Thr Lys Cys Asn Pro Met Gly Tyr Thr Lys Glu Gly Cys Arg Gly Ile
    210                 215                 220

Asp Lys Arg His Trp Asn Ser Gln Cys Arg Thr Thr Gln Ser Tyr Val
225                 230                 235                 240

Ala Arg Gly Ala Leu Thr Met Asp Ser Lys Lys Arg Ile Gly Trp Arg
                245                 250                 255

Phe Ile Arg Ile Asp Thr Ser Cys Val Cys Thr Leu Thr Ile Lys Arg
            260                 265                 270

Gly Arg

<210> SEQ ID NO 10
<211> LENGTH: 271
<212> TYPE: PRT
<213> ORGANISM: Unknown
<220> FEATURE:
<223> OTHER INFORMATION: Pig

<400> SEQUENCE: 10

Pro Val Phe Cys Leu Val Ser Ala Phe Ser Leu Gln Phe His Gln Val
 1               5                  10                  15

Arg Arg Val Met Thr Ile Leu Phe Leu Thr Met Val Ile Ser Tyr Phe
             20                  25                  30

Gly Cys Met Lys Ala Ala Pro Met Lys Glu Ala Asn Val Arg Gly Gln
             35                  40                  45
```

```
Gly Ser Leu Ala Tyr Pro Gly Val Arg Thr His Gly Thr Leu Glu Ser
         50                  55                  60

Val Asn Gly Pro Lys Ala Gly Ser Arg Gly Leu Thr Ser Ser Ser Ser
 65                  70                  75                  80

Ser Ser Leu Ala Asp Thr Phe Glu His Val Ile Glu Glu Leu Leu Asp
                 85                  90                  95

Glu Asp Gln Lys Val Arg Pro Asn Glu Glu Asn Asn Lys Asp Ala Asp
            100                 105                 110

Met Tyr Thr Ser Arg Val Met Leu Ser Ser Gln Val Pro Leu Glu Pro
            115                 120                 125

Pro Leu Leu Phe Leu Leu Glu Glu Tyr Lys Asn Tyr Leu Asp Ala Ala
            130                 135                 140

Asn Met Ser Met Arg Val Arg Arg His Ser Asp Pro Ala Arg Arg Gly
145                 150                 155                 160

Glu Leu Ser Val Cys Asp Ser Ile Ser Glu Trp Val Thr Ala Ala Asp
                165                 170                 175

Lys Lys Thr Ala Val Asp Met Ser Gly Gly Thr Val Thr Val Leu Glu
            180                 185                 190

Lys Val Pro Val Ser Lys Gly Gln Leu Lys Gln Tyr Phe Tyr Glu Thr
            195                 200                 205

Lys Cys Asn Pro Met Gly Tyr Thr Lys Glu Gly Cys Arg Gly Ile Asp
210                 215                 220

Lys Arg His Trp Asn Ser Gln Cys Arg Thr Thr Gln Ser Tyr Val Arg
225                 230                 235                 240

Ala Leu Thr Met Asp Ser Lys Lys Arg Ile Gly Trp Arg Phe Ile Arg
                245                 250                 255

Ile Asp Thr Ser Cys Val Cys Thr Leu Thr Ile Lys Arg Gly Arg
            260                 265                 270

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
ggctgacact ttcgaacac                                              19

<210> SEQ ID NO 12
<211> LENGTH: 40
<212> TYPE: DNA
<213> ORGANISM: Artificial Sequence
<220> FEATURE:
<223> OTHER INFORMATION: Primer

<400> SEQUENCE: 12
tgtaaaacga cggccagtct tgacatcatt ggctgacact                       40

<210> SEQ ID NO 13
<211> LENGTH: 45
<212> TYPE: DNA
<213> ORGANISM: Artificial Sequence
<220> FEATURE:
<223> OTHER INFORMATION: Primer

<400> SEQUENCE: 13
taatacgact cactataggg gtacaagtct gcgtccttat tgttt                 45
```

BDNF POLYMORPHISM AND ASSOCIATION WITH BIPOLAR DISORDER

RELATED APPLICATION

This application claims benefit of U.S. Provisional application 60/148,389, filed Aug. 11, 1999, the entire teachings of which are incorporated herein by reference.

BACKGROUND OF THE INVENTION

Modem psychiatry typically subdivides mood disorders into bipolar disorders (episodes of mania or both mania and depression) and unipolar depressive disorder (episodes of depression). Symptoms of mania include expansive, elevated or irritable mood, inflated self-esteem, grandiosity, decreased need for sleep, increased talkativeness, racing thoughts, distractibility, increased goal-directed activity, and excessive involvement in pleasurable activities with a high potential for painful consequences. Depressive symptoms include depressed mood, diminished interest or pleasure in activities, insomnia or hypersomnia, psychomotor agitation or retardation, fatigue or loss of energy, feelings of worthlessness, excessive guilt, inability to concentrate or act decisively, and recurrent thoughts of death or suicide. Several mental disorders have been proposed as alternate expressions of a bipolar genotype, including variants of schizoaffective disorder, recurrent unipolar depression and hypomania (bipolar II disorder).

Neuropsychiatric disorders, such as schizophrenia, attention deficit disorders, schizoaffective disorders, bipolar disorders and unipolar disorders, differ from neurological disorders in that anatomical or biochemical pathologies are readily detectable for the latter but not the former. Largely as a result of this difference, drugs which have been used to treat individuals with neuropsychiatric disorders, including lithium salts, valproic acid and carbamazepine, have not been predictably effective in treatment regimens across a variety of patients. Treatment regimens are further complicated by the fact that clinical diagnosis currently relies on clinical observation and subjective reports. Identification of the anatomical or biochemical defects which result in neuropsychiatric disorders is needed in order to effectively distinguish between the disorders and to allow the design and administration of effective therapeutics for these disorders.

SUMMARY OF THE INVENTION

As described herein, it has been discovered that a polymorphism in the gene for brain-derived neurotrophic factor (BDNF) is negatively correlated with incidence of neuropsychiatric disorders (e.g., bipolar disorder). In particular, it has been discovered that one or more single nucleotide polymorphisms within the nucleotide sequence encoding the 132 amino acid prepro portion of the BDNF gene product is correlated with reduced incidence of bipolar disorder in a sample population assessed as described herein. In one embodiment, a single nucleotide polymorphism from G to A at nucleotide position 424, resulting in an amino acid change from valine to methionine at amino acid position −63 (relative to the start of the mature protein), is correlated with a reduced incidence of bipolar disorder in the sample population assessed as described herein. That is, it has been determined that there is a variation from random (i.e., that which would be expected by chance) in the transmission of the reference (G) and variant (A) alleles from a parent who is heterozygous for the BDNF alleles to an offspring diagnosed with bipolar disorder. The variant allele (A) is transmitted less frequently (34 of 98 times) to the bipolar offspring than would be expected by chance, while the reference allele (G) is transmitted more frequently (64 of 98 times) than would be expected by chance (p=0.004). Thus, it appears that the variant allele may contribute to protection or reduction in symptomology with respect to bipolar disorder. Alternatively, this particular polymorphism may be one of a group of two or more polymorphisms in the BDNF gene which contributes to the presence, absence or severity of the neuropsychiatric disorder, e.g., bipolar disorder.

Accordingly, the invention relates to methods for diagnosing and treating neuropsychiatric disorders, especially bipolar disorder, and to methods for identifying compounds for use in the diagnosis and treatment of neuropsychiatric disorders. The invention relates to novel compounds and pharmaceutical compositions for use in the diagnosis and treatment of neuropsychiatric disorders. The invention further relates to kits for use in diagnosing neuropsychiatric disorders. In a preferred embodiment, the neuropsychiatric disorder is bipolar disorder.

In one embodiment, the invention relates to a method for predicting the likelihood that an individual will have a neuropsychiatric disorder (or aiding in the diagnosis of a neuropsychiatric disorder), e.g., bipolar disorder, comprising the steps of obtaining a DNA sample from an individual to be assessed and determining the nucleotide present at nucleotide position 424 of the BDNF gene. The presence of an "A" (the variant nucleotide) at position 424 indicates that the individual has a lower likelihood of having a neuropsychiatric disorder than an individual having a "G" at that position, or a greater likelihood of having less severe symptomology. In a preferred embodiment, the neuropsychiatric disorder is bipolar disorder. In a particular embodiment, the individual is an individual at risk for development of bipolar disorder.

In another embodiment, the invention relates to pharmaceutical compositions comprising a variant BDNF gene product for use in the treatment of neuropsychiatric disorders. In one embodiment, the gene product is a peptide comprising amino acids −1 through −132, or a functional portion thereof, of a variant BDNF gene product for use in the treatment of neuropsychiatric disorders. The invention further relates to the use of compositions (i.e., agonists and antagonists) which enhance or increase or which reduce or decrease, respectively, the activity of a peptide comprising amino acids −1 through −132, or a functional portion thereof, of a variant BDNF gene product for use in the treatment of neuropsychiatric disorders. The invention also relates to the use of a nucleic acid molecule encoding a variant BDNF gene product for use in the treatment of neuropsychiatric disorders. In one embodiment, the gene product is a peptide comprising amino acids −1 through −132, or a functional portion thereof, of a variant BDNF gene product. In a particular embodiment the neuropsychiatric disorder is bipolar disorder.

In another embodiment, the invention relates to a method for predicting the likelihood that an individual will have a neuropsychiatric disorder by determining the presence of prepro BDNF or fragment thereof containing the reference or variant amino acid at position −63. The method comprises obtaining a sample from an individual to be assessed, wherein the sample comprises prepro BDNF protein or fragment thereof, wherein said fragment includes amino acid −63 of prepro BDNF protein. The amino acid present at amino acid −63 of said prepro BDNF is determined, wherein the presence of an methionine at position −63 indicates that the individual has a lower likelihood of developing a neuropsychiatric disorder than an individual having a valine at that position. In one embodiment, the amino acid present at amino acid −63 is determined by contacting the sample with an antibody specific for prepro BDNF or fragment thereof containing the reference amino acid. In another embodiment, the amino acid present at amino acid −63 is determined by contacting the sample with an antibody specific for prepro BDNF or fragment thereof containing the variant amino acid.

In another embodiment, the invention is drawn to a method of predicting the likelihood that an individual will have reduced symptomology associated with a neuropsychiatric disorder, comprising determining the presence of prepro BDNF or fragment thereof containing the reference or variant amino acid as described above. The presence of an methionine at position −63 indicates that the individual has a greater likelihood of having reduced symptomology associated with a neuropsychiatric disorder than an individual having a valine at that position.

The invention is also drawn to kits for use the methods of the present invention. In one embodiment, the kit comprises a nucleic acid probe, wherein said probe allows the identification of the nucleotide at position 424 of the BDNF gene. The kit can also include control nucleic acid samples. The control nucleic acid samples can include, for example, the homozygous reference genotype, homozygous variant genotype and the heterozygous genotype at nucleotide position 424 of the BDNF gene. In one embodiment the kit comprises control nucleic acid samples representing the genotype of at least one of the group consisting of: an individual homozygous for a "A" at nucleotide position 424 of a BDNF gene, an individual homozygous for a "G" at nucleotide position 424 of a BDNF gene and an individual heterozygous for said position. In one embodiment, the kit comprises a probe that is an SBE-FRET primer. In more specific embodiment, the probe comprises SEQ ID NO: 11.

In another embodiment, the kit comprises at least one antibody, selected from the group consisting of: an antibody specific for a prepro portion of BDNF or fragment thereof, wherein said prepro portion of BDNF or fragment thereof comprises a methionine at amino acid position −63 and an antibody specific for a prepro portion or fragment thereof of BDNF, wherein said prepro portion or fragment there comprises a valine at amino acid position −63. The kit can also comprise control protein samples representing the genotype of at least one of the group consisting of: an individual homozygous for a nucleic acid sequence encoding a methionine at amino acid position −63 of prepro BDNF protein, an individual homozygous for a nucleic acid sequence encoding a valine at amino acid position −63 of prepro BDNF protein and an individual heterozygous for said position.

BRIEF DESCRIPTION OF THE DRAWINGS

FIGS. 1A and 1B are an illustration (from Maisonpierre et al., *Genomics* 10:558–568 (1991)) of the nucleotide and amino acid sequences of the human and rat BDNF genomic and cDNA clones compared to the pig and mouse cDNA sequences, wherein the sequences are read as shown by the arrows.

Figure 4:
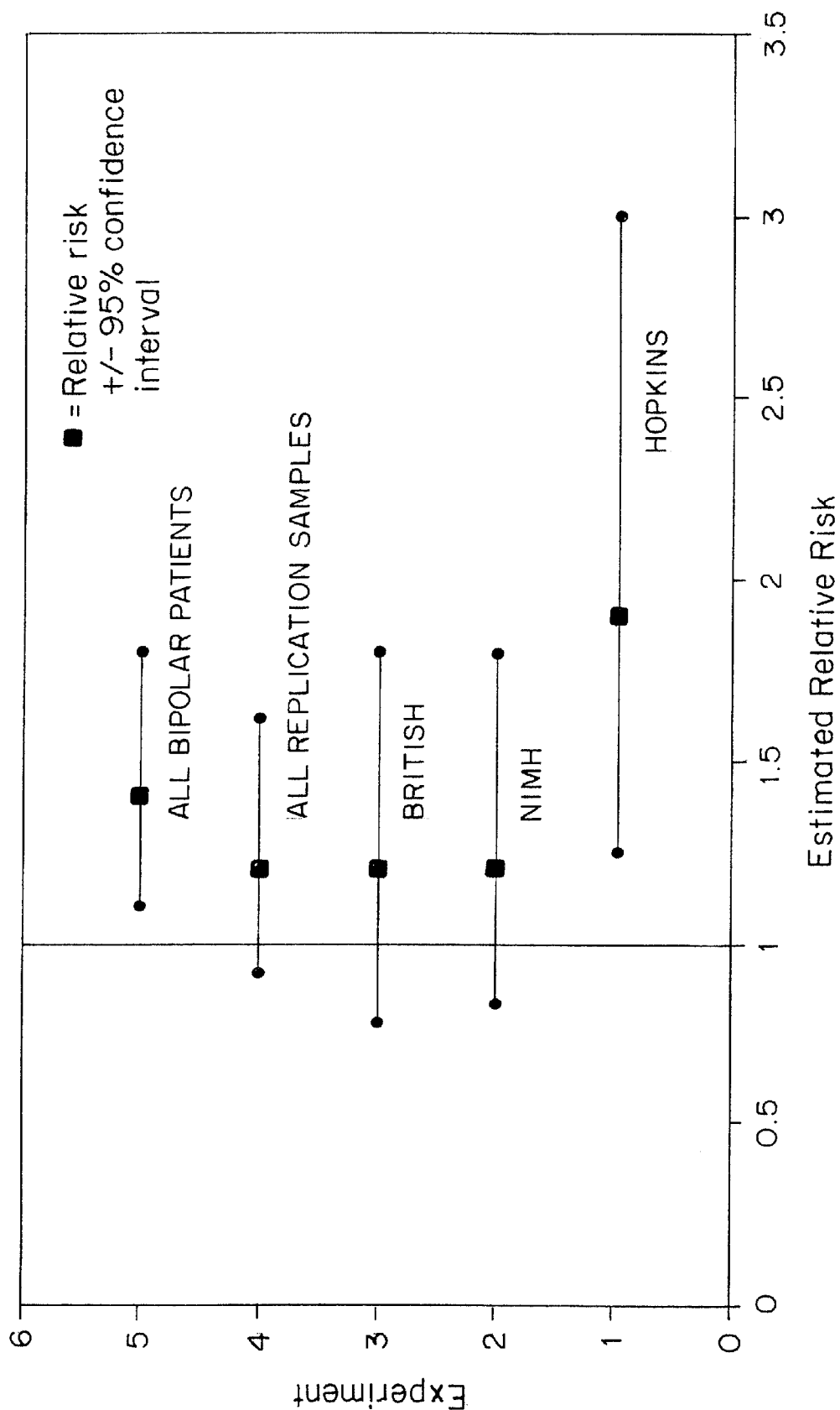

SEQ ID NO: 2 is the human BDNF cDNA sequence exactly as shown in FIGS. 1A and 1B. However, the numbering of both the genomic and cDNA sequences of human BDNF, shown in FIGS. 1A and 1B, accounts for nucleotide sequence of the BDNF gene which is not shown in FIGS. 1A and 1B (intronic portions of the sequence). Thus, position 424 of the human BDNF cDNA, as numbered in FIGS. 1A and 1B, corresponds to nucleotide position 404 of the identical sequence presented in SEQ ID NO: 2.

FIGS. 2A–2E show data resulting from a genotyping assessment of the reference and variant alleles of BDNF in a group of trios having one or more bipolar offspring as described in the Examples.

FIGS. 2F–2J show data resulting from a genotyping assessment of the reference and variant alleles of BDNF in a group of trios having one or more bipolar offspring as described in the Examples.

FIGS. 3A–3C show the data resulting from a genotyping assessment of the reference and variant alleles of BDNF in an additional group of trios having one or more bipolar offspring as described in the Examples.

FIG. 4 shows the estimated relative risk of developing bipolar disorder based on data and analyses from the indicated groups of affected individuals and described in the Exemplification.

DETAILED DESCRIPTION OF THE INVENTION

The development and maintenance of the vertebrate nervous system depends, in part, on the physiological availability of neuronal survival proteins known as neurotrophic factors. Neurotrophic factors play a role in maintaining neurons and their differentiated phenotypes in the adult nervous system. Nerve growth factor (NGF) remains the best characterized neurotrophic factor. However, brain-derived neurotrophic factor (BDNF) has been cloned and shown to be homologous to NGF (Leibrock et al., *Nature* 341:149–152 (1989); Hofer et al., *EMBO J.* 9:2459–2464 (1990); Maisonpierre et al., *Genomics* 10:558–568 (1991)). BDNF is initially synthesized as a 251 amino acid protein precursor that is subsequently cleaved to yield the mature protein. The mature form of BDNF essentially corresponds to the C-terminal half of its precursor and comprises 119 amino acids. In the developing rat, BDNF expression undergoes an increase from initially low levels, and in the adult rat central nervous system, BDNF is expressed at its highest level in the hippocampus. Expression of BDNF is detectable in adult tissues outside of the central nervous system only in heart, lung and skeletal muscle (Maisonpierre et al., *Science* 247:1446–1451 (1990); Hofer et al., *EMBO J.* 9:2459–2464 (1990)).

As shown in FIGS. 1A and 1B, the human genomic sequence of BDNF is SEQ ID NO: 1, the human cDNA sequence is SEQ ID NO: 2, the rat genomic sequence is SEQ ID NO: 3, the rat cDNA sequence is SEQ ID NO: 4, the mouse cDNA sequence is SEQ ID NO: 5, and the pig cDNA sequence is SEQ ID NO: 6. The human amino acid sequence is SEQ ID NO: 7, the rat amino acid sequence is SEQ ID NO: 8, the mouse amino acid sequence is SEQ ID NO: 9, and the pig amino acid sequence is SEQ ID NO: 10. Sequences are designated with a lowercase letter signifying species, an uppercase "B" for BDNF, and a G or a C in parentheses distinguishing between either a genomic or cDNA source for the sequence. DNA sequence identities to the top human sequence are indicated by a dot, and gaps are indicated by a dash. In-frame stop codons in the upstream regions are underlined. Amino acid translation is indicated above the human nucleotide sequence; only amino acid differences with the human sequence are indicated for the other sequences. Amino acids are numbered with position +1 assigned to the first residue in the mature protein sequence. RNA splice sites (SPLICE1 and SPLICE2), the B start site, the consensus protein glycosylation signal, and the consensus protein cleavage signal involved in release of the mature BDNF are indicated. Only sequence flanking splice site 1 is shown for the human and rat genomic clones, since this is the only region in which they differ from their respective cDNA sequences. An exception to this is the presence of a single mismatch (A for G) between the human BDNF genomic and cDNA sequence at nucleotide position 424, resulting in the substitution of a methionine residue for a valine residue at amino acid position −63 in the genomic-derived protein sequence.

As used herein, polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair, in which case it is referred to as a single nucleotide polymorphism.

As described herein, it has been discovered that a polymorphism in the gene for BDNF is negatively correlated with incidence of neuropsychiatric disorders (e.g., bipolar disorder). In particular, it has been discovered that one or more single nucleotide polymorphisms within the nucleotide sequence encoding the 132 amino acid prepro portion of the BDNF gene product are correlated with a reduced incidence of bipolar disorder in the sample population assessed as described herein. In one embodiment, a single polymorphism from G to A at nucleotide position 424 in FIG. 1, or at a nucleotide position corresponding thereto, resulting in an amino acid change from valine to methionine at amino acid position −63 (relative to the start of the mature protein; see FIG. 1), or at an amino acid position corresponding thereto, is correlated with a reduced incidence of bipolar disorder in the sample population assessed as described herein. This polymorphism resides within the 132 amino acid precursor portion (the prepro portion) which is cleaved from the mature protein.

Data from the work described herein has shown that there is a variation from random (i.e., that which would be expected by chance) in the transmission of the reference (G) and variant (A) alleles from a parent who is heterozygous for the BDNF alleles to an offspring diagnosed with bipolar disorder. The variant allele (A) is transmitted less frequently (34 of 98 times) to the bipolar offspring than would be expected by chance, while the reference allele (G) is transmitted more frequently (64 of 98 times) than would be expected by chance (p=0.004). Thus, it appears that the variant allele may contribute to protection or reduction in symptomology with respect to bipolar disorder. Alternatively, this particular polymorphism may be one of a group of two or more polymorphisms in the BDNF gene which contributes to the presence, absence or severity of the neuropsychiatric disorder, e.g., bipolar disorder.

Thus, the invention relates to a method for predicting the likelihood that an individual will have a neuropsychiatric disorder, or for aiding in the diagnosis of a neuropsychiatric disorder, e.g., bipolar disorder, or a greater likelihood of having reduced symptomology associated with a neuropsychiatric disorder, e.g., bipolar disorder, comprising the steps of obtaining a DNA sample from an individual to be assessed and determining the nucleotide present at nucleotide position 424 of the brain-derived neurotrophic factor (BDNF) gene. The presence of an "A" (the variant nucleotide) at position 424 indicates that the individual has a lower likelihood of having a neuropsychiatric disorder, or a greater likelihood of having reduced symptomology associated with a neuropsychiatric disorder, than if that individual had the reference nucleotide at that position. Conversely, the presence of a "G" (the reference nucleotide) at position 424 indicates that the individual has a greater likelihood of having a neuropsychiatric disorder, or a likelihood of having increased symptomology associated with a neuropsychiatric disorder, than if that individual had the variant nucleotide at that position. In a preferred embodiment, the neuropsychiatric disorder is bipolar disorder. In a particular embodiment, the individual is an individual at risk for development of bipolar disorder. In another embodiment the individual exhibits clinical symptomology associated with bipolar disorder. In one embodiment, the individual has been clinically diagnosed as having bipolar disorder.

The genetic material to be assessed can be obtained from any nucleated cell from the individual. For assay of genomic DNA, virtually any biological sample (other than pure red blood cells) is suitable. For example, convenient tissue samples include whole blood, semen, saliva, tears, urine, fecal material, sweat, skin and hair. For assay of cDNA or mRNA, the tissue sample must be obtained from an organ in which the target nucleic acid is expressed. For example, cells from the central nervous system (such as cells of the hippocampus), neural crest-derived cells, skin, heart, lung and skeletal muscle are suitable sources for obtaining cDNA for the BDNF gene. Neural crest derived cells include, for example, melanocytes and keratinocytes.

Many of the methods described herein require amplification of DNA from target samples. This can be accomplished by e.g., PCR. See generally *PCR Technology: Principles and Applications for DNA Amplification* (ed. H. A. Erlich, Freeman Press, New York, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The nucleotide which occupies the polymorphic site of interest (e.g., nucleotide position 424 in BDNF) can be identified by a variety methods, such as Southern analysis of genomic DNA; direct mutation analysis by restriction enzyme digestion; Northern analysis of RNA; denaturing high pressure liquid chromatography (DHPLC); gene isolation and sequencing; hybridization of an allele-specific oligonucleotide with amplified gene products; single base extension (SBE); or analysis of the BDNF protein. In a preferred embodiment, determination of the allelic form of BDNF is carried out using SBE-FRET methods as described in the examples, or using chip-based oligonucleotide arrays. A sampling of suitable procedures are discussed below in turn.

1. Allele-Specific Probes

The design and use of allele-specific probes for analyzing polymorphisms is described by e.g., Saiki et al., *Nature* 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25–30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some examples of which are described in WO 95/11995. WO 95/11995 also describes subarrays that are optimized for detection of a variant form of a precharacterized polymorphism. Such a subarray contains probes designed to be complementary to a second reference sequence, which is an allelic variant of the first reference sequence. The second. group of probes is designed by the same principles, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarity. See Gibbs, *Nucleic Acid Res.* 17, 2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

4. Direct-Sequencing

The direct analysis of the sequence of polymorphisms of the present invention can be accomplished using either the dideoxy chain termination method or the Maxam-Gilbert method (see Sambrook et al., *Molecular Cloning, A Laboratory Manual* (2nd Ed., CSHP, New York 1989); Zyskind et al., *Recombinant DNA Laboratory Manual,* (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., *PCR Technology, Principles and Applications for DNA Amplification,* (W. H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., *Proc. Nat. Acad. Sci.* 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence differences between alleles of target sequences.

The polymorphism of the invention may contribute to the protection of an individual against bipolar disorder in different ways. The polymorphism may contribute to phenotype by affecting protein structure. By altering amino acid sequence, the polymorphism may alter the function of the encoded protein. The polymorphism may exert phenotypic effects indirectly via influence on replication, transcription, and translation. For example, the substitution of a methionine for a valine in the prepro portion of the BDNF gene product may create an alternative translation start site which alters the length of the gene product and the prepro portion itself. Alteration of the length of the gene product may affect cleavage of the mature protein either positively or negatively. Alternatively, the presence of the variant amino acid may alter the properties of the gene product so as to alter cleavage of the gene product. More than one phenotypic trait may be affected. For example, other neuropsychiatric disorders which are believed to be alternate expressions of a bipolar genotype, including variants of schizoaffective disorder, recurrent unipolar depression and hypomania (bipolar II disorder), may also be affected by the BDNF polymorphism described herein. Additionally, the described polymorphism may predispose an individual to a distinct mutation that is causally related to a certain phenotype, such as susceptibility or resistance to bipolar disorder. The discovery of the polymorphism and its correlation with bipolar disorder facilitates biochemical analysis of the variant and the development of assays to characterize the variant and to screen for pharmaceuticals that interact directly with one or another form of the protein.

Alternatively, this particular polymorphism may be one of a group of two or more polymorphisms in the BDNF gene which contributes to the presence, absence or severity of the neuropsychiatric disorder, e.g., bipolar disorder. An assessment of other polymorphisms within the BDNF gene can be undertaken, and the separate and combined effects of these polymorphisms on the neuropsychiatric disorder phenotype can be assessed.

Correlation between a particular phenotype, e.g., the bipolar phenotype, and the presence or absence of a particular allele is performed for a population of individuals who have been tested for the presence or absence of the phenotype. Correlation can be performed by standard statistical methods such as a Chi-squared test and statistically significant correlations between polymorphic form(s) and phenotypic characteristics are noted. For example, as described herein, it has been found that the presence of the BDNF variant allele, having an A at polymorphic site 424, correlates negatively with bipolar disorder with a p value of p=0.004 by Chi-squared test.

This correlation can be exploited in several ways. In the case of a strong correlation between a particular polymorphic form, e.g., the reference allele for BDNF, and a disease for which treatment is available, e.g., bipolar disorder, detection of the polymorphic form in an individual may justify immediate administration of treatment, or at least the institution of regular monitoring of the individual. Detection of a polymorphic form correlated with a disorder in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic form and a particular disorder, immediate therapeutic intervention or monitoring may not be justified. Nevertheless, the individual can be motivated to begin simple life-style changes (e.g., therapy or counseling) that can be accomplished at little cost to the individual but confer potential benefits in reducing the risk of conditions to which the individual may have increased susceptibility by virtue of the particular allele. Furthermore, identification of a polymorphic form correlated with enhanced receptiveness to one of several treatment regimes for a disorder indicates that this treatment regime should be followed for the individual in question.

Furthermore, it may be possible to identify a physical linkage between a genetic locus associated with a trait of interest (e.g., bipolar disorder) and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., *Proc. Natl. Acad. Sci. (USA)* 83, 7353–7357 (1986); Lander et al., *Proc. Natl. Acad. Sci. (USA)* 84, 2363–2367 (1987); Donis-Keller et al., *Cell* 51, 319–337 (1987); Lander et al., *Genetics* 121, 185–199 (1989)). Genes localized by linkage can be cloned by a process known as directional cloning. See Wainwright, *Med. J. Australia* 159, 170–174 (1993); Collins, *Nature Genetics* 1, 3–6 (1992).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., *Science* 245, 1073–1080 (1989); Monaco et al., *Nature* 316, 842 (1985); Yamoka et al., *Neurology* 40, 222–226 (1990); Rossiter et al., *FASEB Journal* 5, 21–27 (1991).

Linkage is analyzed by calculation of LOD (log of the odds) values. A lod value is the relative likelihood of obtaining observed segregation data for a marker and a genetic locus when the two are located at a recombination fraction $\theta$, versus the situation in which the two are not linked, and thus segregating independently (Thompson & Thompson, *Genetics in Medicine* (5th ed, W. B. Saunders Company, Philadelphia, 1991); Strachan, "Mapping the human genome" in *The Human Genome* (BIOS Scientific Publishers Ltd, Oxford), Chapter 4). A series of likelihood ratios are calculated at various recombination fractions ($\theta$), ranging from $\theta=0.0$ (coincident loci) to $\theta=0.50$ (unlinked). Thus, the likelihood at a given value of $\theta$ is: probability of data if loci linked at $\theta$ to probability of data if loci unlinked. The computed likelihoods are usually expressed as the logso of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of $\theta$ (e.g., LIPED, MLINK (Lathrop, *Proc. Nat. Acad. Sci. (USA)* 81, 3443–3446 (1984)). For any particular lod score, a recombination fraction may be determined from mathematical tables. See Smith et al., *Mathematical tables for research workers in human genetics* (Churchill, London, 1961); Smith, *Ann. Hum. Genet.* 32, 127–150 (1968). The value of $\theta$ at which the lod score is the highest is considered to be the best estimate of the recombination fraction.

Positive lod score values suggest that the two loci are linked, whereas negative values suggest that linkage is less likely (at that value of $\theta$) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of –2 or less is taken as definitive evidence against linkage of the two loci being compared. Negative linkage data are useful in excluding a chromosome or a segment thereof from consideration. The search focuses on the remaining non-excluded chromosomal locations.

In another embodiment, the invention relates to pharmaceutical compositions comprising a variant BDNF gene product. As used herein, a variant BDNF gene product is intended to mean gene products which are encoded by the variant allele of the BDNF gene and includes, but is not limited to, the complete (uncleaved) variant BDNF gene product, the cleaved BDNF protein and the cleaved prepro portion of the gene product. In one embodiment, the gene product is a peptide comprising amino acids –1 through –132 of a variant BDNF gene product, or a functional portion thereof, for use in the treatment of neuropsychiatric disorders. The invention further relates to the use of compositions (i.e., agonists) which enhance or increase the activity of a peptide comprising amino acids –1 through –132 of the variant BDNF gene product, or a functional portion thereof, for use in the treatment of neuropsychiatric disorders. The invention also relates to the use of compositions (i.e., antagonists) which reduce or decrease the activity of a peptide comprising amino acids –1 through –132 of the variant BDNF gene product, or a functional portion thereof, for use in the treatment of neuropsychiatric disorders. In a particular embodiment the neuropsychiatric disorder is bipolar disorder.

In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

For instance, the variant polypeptide or protein, or fragment thereof, of the present invention can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous peptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents and treatment regimens.

Polyclonal and/or monoclonal antibodies that specifically bind one form of the gene product but not to the other form of the gene product are also provided. Antibodies are also provided that bind a portion of either the variant or the reference gene product that contains the polymorphic site. Antibodies can be made by injecting mice or other animals with, for example, the variant gene product or peptide fragments thereof comprising the variant portion. The peptide framents can be synthetically produced or produced in a suitable host cell expressing a nucleic acid encoding said peptide. In another embodiment, the animal is injected with the reference gene product or fragments thereof containing amino acid position −63. Monoclonal antibodies are screened as are described, for example, in Harlow & Lane, *Antibodies, A Laboratory Manual,* Cold Spring Harbor Press, New York (1988); Goding, *Monoclonal antibodies, Principles and Practice* (2d ed.) Academic Press, New York (1986). Monoclonal antibodies are tested for specific immunoreactivity with, for example, a variant gene product and lack of immunoreactivity to the corresponding prototypical gene product. In another embodiment, antibodies are produced and tested for specific immunoreactivity to the reference gene product and lack of immunoreactivity to the variant gene product. These antibodies are useful in diagnostic assays for detection of the variant form, or as an active ingredient in a pharmaceutical composition.

The invention further relates to a method of diagnosing or aiding in the diagnosis of a disorder associated with the presence of all or a portion of the prepro BDNF protein in an individual. The method comprises obtaining a biological sample containing the prepro BDNF protein or relevant portion thereof from the individual and determining the amino acid present at amino acid position −63 relative to the first amino acid of the mature protein. Wherein the presence of the reference amino acid, valine at this position is indicative of increased likelihood of the disorder in the individual as compared with an appropriate control, e.g., an individual having the variant amino acid at position −63. In one embodiment, the prepro portion of BDNF from an individual is analyzed.

In one embodiment, the method comprises obtaining a biological sample containing the prepro BDNF protein or relevant portion thereof from the individual and determining the amino acid present at position −63 relative to the first amino acid of the mature protein, wherein presence of a variant amino acid, e.g., methionine, at said position is indicative of decreased likelihood of the disorder in the individual as compared with an appropriate control, e.g., an individual having the reference (valine) amino acid said position. In one embodiment, the prepro portion of BDNF is analyzed.

In one embodiment, the invention relates to a method for predicting the likelihood that an individual will have a bipolar disorder (or aiding in the diagnosis of a bipolar disorder), comprising the steps of obtaining a biological sample comprising the prepro BDNF protein or fragment thereof containing amino acid position −63 from an individual to be assessed and determining the amino acid present at amino acid position −63. The presence of the variant amino acid at this position indicates that the individual has a lower likelihood of having a bipolar disorder than an individual having the reference amino acid at this position, or a lower likelihood of having severe symptomology. In a particular embodiment, the individual is an individual at risk for development of bipolar disorder.

The invention also relates to a method for predicting the likelihood that an individual will have a bipolar disorder, or for aiding in the diagnosis of a bipolar disorder, or predicting the likelihood of having altered symptomology associated with a bipolar disorder, comprising the steps of obtaining a biological sample comprising prepro BDNF protein or fragment thereof containing amino acid position −63 from an individual to be assessed and determining the amino acid present at amino acid positions −63 of the prepro BDNF gene product. For example, the prepro region of the BDNF can be cleaned from or linked to the mature BDNF protein. As used herein, the term "fragment thereof" of the prepro BDNF protein is intended to encompass any portion of the protein which comprises the polymorphic amino acid position. The presence of valine at position −63 indicates that the individual has a greater likelihood of having bipolar disorder, or a greater likelihood of having severe symptomology associated with a bipolar disorder, than if that individual had a variant amino acid at this position. Conversely, the presence of methionine indicates that the individual has a reduced likelihood of having a bipolar disorder or a likelihood of having reduced symptomology associated with a bipolar disorder, than if that individual had the reference amino acid at this position.

In a particular embodiment, the individual is an individual at risk for development of a bipolar disorder. In another embodiment the individual exhibits clinical symptomology associated with a bipolar disorder. In one embodiment, the individual has been clinically diagnosed as having a bipolar disorder.

In this embodiment of the invention, the biological sample contains protein molecules from the test subject. As described above for BDNF cDNA or mRNA, suitable sources for the biological sample are any tissue or bodily fluid that is expected to express or contain prepro BDNF protein or the prepro portion of BDNF can be used. In vitro techniques for detection of protein of interest include enzyme linked immunosorbent assays (ELISAs), Western blots, immunoprecipitations and immunofluorescence. Furthermore, in vivo techniques for detection of protein include introducing into a subject a labeled anti-protein antibody. For example, the antibody can be labeled with a radioactive marker whose presence and location in a subject can be detected by standard imaging techniques. Polyclonal and/or monoclonal antibodies that specifically bind to variant gene products but not to corresponding reference gene products, and vice versa, are also provided. Antibodies can be made as described above. These antibodies are useful in diagnostic assays for detection of the variant form, or as an active ingredient in a pharmaceutical composition.

The invention also encompasses kits for detecting the presence of proteins or nucleic acid molecules of the invention in a biological sample. For example, the kit can comprise a labeled compound or agent (e.g., nucleic acid probe such as SEQ ID NO: 11,) capable of detecting protein or mRNA (or cDNA produced from the mRNA) in a biological sample; means for determining the identity of nucleotide 424 of the BDNF gene in the mRNA corresponding mRNA in the sample or the amino acid identity at position −63 of the prepro portion of BDNF in the sample; and means for comparing said identities of mRNA in the sample with a suitable standard. The kit can also comprise control samples for use as standards, representing individuals homozygous for the reference or variant nucleotide in the case of analyzing nucleic acid, or the reference or variant amino acid in the case of analyzing proteins, or representing a heterozygous individual. For the detection of the reference or the variant prepro portion of BDNF, the kit can contain antibodies specific for either the reference or the variant prepro portion of BDNF together with suitable regents to detect antibody binding to its target antigen. The compound or agent can be packaged in a suitable container. The kit can further comprise instructions for using the kit to detect protein or nucleic acid.

The invention further pertains to compositions, e.g., vectors, comprising a nucleotide sequence encoding variant BDNF gene product. In one embodiment, the gene product is a peptide comprising amino acids −1 through −132 of the variant BDNF gene product, or a functional portion thereof, for use in the treatment of neuropsychiatric disorders. For example, variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli,* yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like.

It is also contemplated that cells can be engineered to express the variant BDNF allele of the invention by gene therapy methods. For example, DNA encoding the variant BDNF gene product, or an active fragment or derivative thereof, can be introduced into an expression vector, such as a viral vector, and the vector can be introduced into appropriate cells in an animal. In such a method, the cell population can be engineered to inducibly or constitutively express active variant BDNF gene product. In a preferred embodiment, the vector is delivered to the bone marrow, for example as described in Corey et al. (*Science* 244:1275–1281 (1989)).

The invention further provides transgenic nonhuman animals capable of expressing an exogenous variant BDNF gene and/or having one or both alleles of an endogenous variant BDNF gene inactivated. Expression of an exogenous variant gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous variant genes can be achieved by forming a transgene in which a cloned variant gene is inactivated by insertion of a positive selection marker. See Capecchi, *Science* 244, 1288–1292 (1989). The transgene is then introduced into an embryonic stem cell, where it undergoes homologous recombination with an endogenous variant gene. Mice and other rodents are preferred animals. Such animals provide useful drug screening systems.

The invention will be further illustrated by the following non-limiting examples. The teachings of the references cited herein are incorporated herein by reference in their entirety.

EXAMPLES

Sample Population

A sample population of 150 trios was initially assessed by genotyping methods for heterozygousity with respect to the BDNF reference and variant alleles as described herein. A trio included two parents and an offspring diagnosed as having bipolar disorder according to the American Psychiatric Association's Diagnostic and Statistical Manual of Mental Disorders. Of the 150 trios assessed, 98 of these trios had at least one parent who was heterozygous for the BDNF reference and variant alleles; these 98 trios were selected for further study, as the heterozygousity of the parent allowed a determination of which allele the parent transmitted to the bipolar offspring. The bipolar offspring in the trios were assessed by genotyping methods to determine which BDNF allele had been transmitted to them by the heterozygous parent. In instances where two parents had two offspring diagnosed with bipolar disorder, each trio (i.e., two parents and one offspring) was considered individually.

SBE-FRET Protocol

The genotyping method used for these studies was based on single-base extension (SBE) and fluorescence resonance energy transfer (FRET). A locus-specific primer (FRET primer; 5'-GGCTGACACTTTCGAACAC (SEQ ID NO: 11) was ordered 5' labeled with FAM. The primer was designed so that the 3' end was one base 5' to the polymor phic site of interest (e.g., nucleotide 424). The locus of interest was amplified and single base extension of the FRET primer was performed with fluorescently labeled ddNTPs in dye-terminator sequencing fashion, except that no deoxyribonucleotides are present. PCR primers were:

Forward PCR primer 5'-TGTAAAACGACGGCCAGTCTTGACATCATT GGCTGACACT (SEQ ID NO: 12); and Reverse PCR primer 5'-TAATACGACTCACTATAGGGGTACAAGTCT GCGTCCTTATTGTTT (SEQ ID NO: 13).

The ddNTP corresponding to the variant base (A) was labeled with TAMRA, and the reference base (G) was labeled with ROX. Depending on the genotype of the individual, the FRET primer was extended with a ROX-labeled or TAMRA-labeled ddNTP. Upon incorporation of either ROX- or TAMRA-labeled ddNTPs, energy transfer occurs between the donor dye (FAM on FRET primer) and the acceptor dye (the ROX- or TAMRA-labeled ddNTP). An increase in the fluorescence intensity of one (for a homozygote) or both (for a heterozygote) of the acceptor dyes was used to infer the genotype of an individual.

Summary of Experimental Procedures Used in the Above-described Analysis.

I Amplify locus of interest
II Clean-up of PCR products with shrimp alkaline phosphate (SAP) and Exonuclease I (EXO)
III Single-base extension/fluorescence detection in AB17700
I Amplification of Locus of Interest—for 96-Well Plate

TABLE I

PCR MIX

| | Each Reaction (µL) | For 96-well plage (µL) |
|---|---|---|
| 10 mM dNTP | 0.05 | 5.2 |
| 10X PCRII buffer | 2.0 | 208 |
| 25 mM MgCl2 | 1.2 | 125 |
| 20 µM PCR primer F | 0.25 | 26 |
| 20 µM PCR primer R | 0.25 | 26 |
| ddH$_2$O | 11.05 | 1149 |
| 5 U/µL Amplitaq-gold | 0.2 | 20.8 |
| | 15 | |

Fifteen microliters of the PCR mix were added to a 96-well MJ plate. Five microliters of genomic DNA (5 ng/µL) were added to the aliquoted PCR mix. (5 µL of 1 ng/µL is often adequate). The plate was sealed with MJ plate-seal 'A'. PCR was conducted using the following program:

96° C.×10 minutes
96° C.×30 seconds, 50C.×1 minute, 72C.×1 minute for 35 cycles
72° C.×10 minutes followed by a hold at 4° C.

II PCR Product Clean-up

TABLE II

SAP/EXO MIX

| | Each reaction (µL) | For 96-well plate (µL) |
|---|---|---|
| Shrimp alkaline phosphatase (1 U/µL) | 1.0 | 104 |

TABLE II-continued

SAP/EXO MIX

| | Each reaction (µL) | For 96-well plate (µL) |
|---|---|---|
| Exonuclease 1 (10 U/µL) | 0.05 | 5.2 |
| 10X SAP buffer | 1.0 | 104 |
| ddH$_2$O | 2.95 | 306.8 |
| | 5.0 | |

Five microliters of SAP/EXO mix were added to a clean MJ plate. Five microliters of the PCR product were added directly to the aliquoted SAP/EXP mix. The PCR plates were spun down and sealed with Microseal A film. The mixture was incubated at 37° C. for 45 minutes and then at 96° C. for 15 minutes.

III Single-base Extension/Fluorescence Detection in ABI7700

(The reactions were carried out in the same MJ plate used for SAP/EXO step, capped with 8-strip MicroAmp optical caps) The ddNTPs that should be incorporated in the genotyping reaction were selected. In this experiment, TAMRA was used to identify the variant base and ROX for the reference base, although other possibilities exist.

TABLE IV

SBE-FRET MIX

| | Each reaction (µL) | For 96-well plate (µL) |
|---|---|---|
| FAM primer (100 uM) | 0.02 | 2.08 |
| ROX ddNTP (100 um) | 0.02 | 2.08 |
| TAMRA ddNTP (100 um) | 0.02 | 2.08 |
| Thermoseq. Buffer (10x) | 2.0 | 208 |
| ddH$_2$O | 7.9 | 821.6 |
| Thermosequenase (32 U/µL) | 0.016 | 1.7 |
| | 10.0 | |

Ten microliters of SBE-FRET mix were added to the MJ plates containing 10 µL SAP/Exo treated PCR products.

The plates were tapped on bench to mix, they can also be spun briefly if necessary.

The wells were capped with optical caps. The capped wells can be rolled with roller if necessary.

The plates were placed in a thermocycling detector apparatus (ABI7700).

The plates were incubated for 6 cycles of (for a 20 µL reaction) as follows:
96° C.×15 seconds
50° C.×30 seconds
60° C.×30 seconds Data were collected in the 60° C. stage using detection settings suitable for measuring TAMRA and ROX fluorescence.

At the end of the run, the plate was saved as "projectname.SBExxx.pyyy", where project name is the project (e.g. cancer), xxx is the number of the polymorphism being genotyped (e.g. 48), and yyy is the plate number (e.g. 04).

To analyze the data, "analyze" was selected under the Analysis menu (command-L). The 7700 apparatus provides a screen to adjust the threshold levels. "0" was input in the "use threshold" box and "2" for cycle number in both the Baseline start and stop boxes. "Update calculations" was selected. The resulting error message box was closed.

The data were exported and analyzed using Excel.

Data were analyzed by plotting ROX fluorescence versus TAMRA fluorescence and comparing the values between samples, control samples containing no template and samples of known geneotype. Typically, homozygous reference controls have little or no TAMRA fluorescence, homozygous variant controls have little or no ROX fluorescence and heterozygous controls have similar TAMRA and ROX fluorescence. Genotypes determined included REF, HET, VAR, FAIL (signal too low) or A-FAIL (ambiguous—signal not within one of the values set above).

Results reference allele (G) is transmitted more frequently (64 of 98 times) than would be expected by chance (p=0.004). In the general population (in which about 0.8 percent of the individuals are diagnosed with bipolar disorder), the variant (A) allele occurs with a frequency of 15 percent, while the reference allele occurs with a frequency of 85 percent. In the sample population assessed as described herein, in which all of the individuals are diagnosed with bipolar disorder, the variant allele occurs with a frequency of 7 percent. Thus, it appears that the variant allele may contribute to protection or reduction in symptomology with respect to bipolar disorder.

FIG. 4 and Table V show data obtained from additional human samples.

TABLE V

| Samples | Trans | Untrans. | p val | # trans | relative risk | 95% CF | # trios |
|---|---|---|---|---|---|---|---|
| Hopkins | 55 | 29 | 0.0023 | 84 | 1.90 | 1.25–3.0 | 127 |
| U01 + NIMH | 50 | 42 | 0.2021 | 92 | 1.19 | 0.83–1.8 | 155 |
| British | 38 | 32 | 0.2366 | 70 | 1.19 | 0.77–1.8 | 145 |
| all repl. | 88 | 74 | 0.1357 | 162 | 1.19 | 0.91–1.8 | 300 |
| all BP | 143 | 103 | 0.0054 | 246 | 1.39 | 1.1–1.8 | 427 |

Data from the work described herein has shown that there is a variation from random (i.e., that which would be expected by chance) in the transmission of the reference (G) and variant (A) alleles from an individual parent who is heterozygous for the BDNF alleles to an offspring diagnosed with bipolar disorder. FIGS. 2A–2J show data resulting from a genotyping assessment of the reference and variant alleles of BDNF in a group of trios having one or more bipolar offspring. Column 1 shows the family reference number for the trio. Column 2 shows the reference number for the individual being assessed. Columns 3 and 4 show the reference number for the father and the mother, respectively, in the trio. Column 5 shows the gender of the individual being assessed. Column 6 shows the genotype of the individual being assessed with respect to BDNF; REF indicates that the individual was homozygous for the reference (G) allele, VAR indicates that the individual was homozygous for the variant allele, HET indicates that the individual was heterozygous, and FAIL indicates that no data was collected for that individual. Columns 7 and 8 show the number of times that the reference and variant allele, respectively, were transmitted to offspring by the heterozygous parent.

FIGS. 3A–3C show data resulting from a genotyping assessment of the reference and variant alleles of BDNF in an additional group of trios having one or more bipolar offspring. Column I shows the family reference number for the trio. Column 2 shows the individual reference number for the individual being assessed. Column 3 shows whether the individual being assessed was the offspring (patient) or parent. Column 4 shows the genotype of the individual being assessed with respect to BDNF; REF indicates that the individual was homozygous for the reference (G) allele, VAR indicates that the individual was homozygous for the variant allele, HET indicates that the individual was heterozygous, and FAIL indicates that no data was collected for that individual. Columns 5 and 6 show the number of times that the reference and variant allele, respectively, were transmitted to offspring by the heterozygous parent.

The data demonstrate that the variant allele (A) is transmitted less frequently (34 of 98 times) to the bipolar offspring than would be expected by chance, while the "Hopkins" refers to a to a group of patients with bipolar disorder obtained in collaboration with Johns Hopkins. "U01 and NIMH" refer to a group of 155 trios some of which are from Johns Hopkins and some are from the Genetics Initiative at the NIMH. "British" refers to 145 trios from 5 collaborators in England.

In Table V, "Trans" is the number of times the allele in question (in this case the reference allele) was transmitted from a heterozygous parents to a bipolar child. "Untrans" is the number of times the other (variant) allele was passed from the heterozygous parent to the bipolar child. The number of trios used is show in the column labeled "#trios" and is the number of trios for which genotypes were available. Not all of the parents were considered to be "informative". To be included in the analysis, the parent in question had to be a heterozygote.

The relative risk (estimated relative risk on FIG. 4) is defined as the transmission ratio in trios (i.e # transmitted alleles/# untransmitted alleles). Under a multiplicative disease model, this is an estimator of genotypic relative risk. The confidence interval was calculated using a binomial distribution.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for predicting the likelihood that an individual will be diagnosed with a bipolar disorder, comprising the steps of:
   a) obtaining a DNA sample from an individual to be assessed; and
   b) determining the nucleotide present at the nucleotide position corresponding to position 404 of SEQ ID NO: 2, wherein the presence of an "A" (adenine) at position 404 indicates that the individual has a lower likelihood of being diagnosed with a bipolar disorder than an individual having a "G" (guanine) at that position.

2. A method according to claim 1, wherein the individual is an individual at risk for development of bipolar disorder.

3. A method for predicting the likelihood that an individual will be diagnosed with a bipolar disorder, comprising the steps of:
   a) obtaining a DNA sample from an individual to be assessed; and
   b) determining the nucleotide present at the nucleotide position corresponding to position 404 of SEQ ID NO: 2, wherein the presence of an "G" (guanine) at position 404 indicates that the individual has a greater likelihood of being diagnosed with a bipolar disorder than an individual having an "A" (adenine) at that position.

4. A method according to claim 1, wherein the individual exhibits clinical symptoms of mania or mania and depression.

5. A method according to claim 3, wherein the individual is an individual at risk for development of bipolar disorder.

6. A method according to claim 3, wherein the individual exhibits clinical symptoms of mania or mania and depression.

* * * * *